United States Patent
Neymann et al.

(10) Patent No.: US 10,872,680 B2
(45) Date of Patent: *Dec. 22, 2020

(54) COMPUTER-IMPLEMENTED METHOD FOR CREATING A FERMENTATION MODEL

(71) Applicant: BAYER AKTIENGESELLSCHAFT, Leverkusen (DE)

(72) Inventors: Tobias Neymann, Bergisch Gladbach (DE); Lukas Hebing, Dortmund (DE); Sebastian Engell, Wetter (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 59 days.

This patent is subject to a terminal disclaimer.

(21) Appl. No.: 16/369,467

(22) Filed: Mar. 29, 2019

(65) Prior Publication Data
US 2019/0228835 A1 Jul. 25, 2019

Related U.S. Application Data

(63) Continuation of application No. 15/009,903, filed on Jan. 29, 2016, now Pat. No. 10,296,708.

(30) Foreign Application Priority Data

Jan. 29, 2015 (EP) ...................................... 15153052

(51) Int. Cl.
*G06G 7/48* (2006.01)
*G16B 5/00* (2019.01)
*G06F 17/10* (2006.01)

(52) U.S. Cl.
CPC ............... *G16B 5/00* (2019.02); *G06F 17/10* (2013.01)

(58) Field of Classification Search
None
See application file for complete search history.

(56) References Cited

U.S. PATENT DOCUMENTS

| | | | |
|---|---|---|---|
| 8,691,552 B2* | 4/2014 | Gonzalez | C12R 1/19 435/252.1 |
| 2004/0033975 A1* | 2/2004 | Fu | G01N 33/5091 514/44 R |
| 2008/0108048 A1 | 5/2008 | Bartee et al. | |
| 2008/0167852 A1 | 7/2008 | Bartee et al. | |
| 2013/0302866 A1* | 11/2013 | Finley | C12Y 604/01001 435/145 |

OTHER PUBLICATIONS

J. Gao et al, "Dynamic Metabolic Modeling for a MAB Bioprocess"; Biotechnology Progress, (2007), 23, pp. 168-181.

Provost A. et al, "Metabolic design of macroscopic bioreaction models: application to Chinese hamster ovary cells"; Bioprocess and Biosystems Engineering (2006), 29, pp. 349-366.

(Continued)

*Primary Examiner* — Rehana Perveen
*Assistant Examiner* — Nithya J. Moll
(74) *Attorney, Agent, or Firm* — McBee Moore & Vanik IP, LLC

(57) ABSTRACT

The application relates to a computer-implemented method for creating a model of bioreaction—fermentation process or whole-cell catalysis process—with an organism on the basis of measured data.

13 Claims, 10 Drawing Sheets

(56) References Cited

OTHER PUBLICATIONS

Frahm B, et al., "Adaptive, Model-Based Control by the Open-Loop-Feedback-Optimal (OLFO) Controller for the Effective Fed-Batch Cultivation of Hybridoma Cells", Biotechnol. Prog. (2002) 18, pp. 1095-1103.

Kontoravdi C, et al., "Development of a dynamic model of monoclonal antibody production and glycosylation for product quality monitoring", Computers & Chemical Engineering 31, 2007, pp. 392-400.

Jedrzejewski PM, et al., "Towards Controlling the Glycoform: A Model Framework Linking Extracellular Metabolites to Antibody Glycosylation", International Journal of Molecular Sciences, 2014, 15, pp. 4492-4522.

Jimenez Del Val, "A dynamic mathematical model for monoclonal antibody N-linked glycosylation and nucleotide sugar donor transport within a maturing Golgi apparatus", Biotechnology progress 27, 2011, pp. 1730-1743.

Leifheit J, et al., "Rechnergestuetzte halbautomatische Modellierung biotechnologischer Prozesse (Semiautomatic Modeling of Biotechnical Processes)", at—Automatisierungstechnik 55(5), 2007, pp. 211-218 [cited on pp. 4, 8, 9 and 10 of the specification].

Provost A., "Metabolic design of dynamic bioreaction models"; Faculte des Sciences Appliquees, Universite Catholique de Louvain, Louvain-la-Neuve, Louvain-la-Neuve, S. 81 ff., S. 107 ff. S. 118 ff, 2006.

Pfeiffer T, et al., "Metatool: for studying metabolic networks"; Bioinformatics 15(3), 1999, pp. 251-257.

Soons, Z. I. T. A., et al., "Selection of elementary modes for bioprocess control", Computer Applications in Biotechnology, Leuven, Belgium, 2010, pp. 156-161.

Leighty, R. W., & Antoniewicz, M. R., "Dynamic metabolic flux analysis (DMFA): a framework for determining fluxes at metabolic non-steady state", Metabolic engineering, 13, 2011, pp. 745-755.

Murtuza Baker, et al., "Comparison of different algorithms for simultaneous estimation of multiple parameters in kinetic metabolic models", J. Integrative Bioinformatics, 7(3):133, 2010, pp. 1-9.

Niu et al. "Metabolic pathway analysis and reduction for mammalian cell cultures—Towards macroscopic modeling", Chemical Engineering Science (2013) 102, S. 1-40.

Baughman et al.; "On the dynamic modeling of mammalian cell metabolism and mAb production"; Computers and Chemical Engineering 34, 2010, pp. 210-222.

Villadsen et al. "Bioreaction engineering principles", Third Edition, Springer Verlag, Chapter 3, Elemental and Redox Balances, pp. 73.

Ruggeri, Bernardo, Tonia Tommasi, and Guido Sassi. "Experimental kinetics and dynamics of hydrogen production on glucose by hydrogen forming bacteria (HFB) culture." International Journal of Hydrogen Energy 34.2 (2009): 753-763.

Yuan, Jingqi, Yinghui Liu, and Jun Geng. "stoichiometric balance based macrokinetic model for Penicillium chrysogenum in fed-batch fermentation." Process Biochemistry 45.4 (2010): 542-548.

Mitchell, David A., et al. "A review of recent developments in modeling of microbial growth kinetics and intraparticle phenomena in solid-state fermentation." Biochemical Engineering Journal 17.1 (2004): 15-26.

* cited by examiner

COMPUTER-IMPLEMENTED METHOD FOR CREATING A FERMENTATION MODEL

CROSS-REFERENCE TO RELATED APPLICATIONS

This application is a continuation of U.S. patent application Ser. No. 15/009,903, filed Jan. 29, 2016, which claims priority to European Patent Application No. 15153052.4, filed Jan. 29, 2015. The disclosures of the priority applications are incorporated in their entirety herein by reference.

The invention relates to a computer-implemented method for creating a model of a bioreaction—especially fermentation or whole-cell catalysis—using an organism.

"Organism" in the sense of the application denotes cultures of plant or animal cells such as mammalian cells, yeasts, bacteria, algae, etc., which are used in bioreactions.

Sensory monitoring of a fermentation process and analysis of samples from a process e.g. by means of the quality-by-design analysis automation platform BaychroMAT® from Bayer Technology Services GmbH provides varied information about the state of the process in the bioreactor in real time. Typically, cell count, cell viability, concentrations of substrates, such as carbon sources (e.g. glucose), amino acids or $O_2$, products and by-products (e.g. lactate or $CO_2$), process parameters such as temperature and/or pH or product features are determined. These data may be supplemented with calculated data and/or extrapolations e.g. from the prior art. Together, these data form the measured data or the process know-how in the sense of the application.

Background knowledge about the organism means, in the sense of the application, knowledge about the organism's biochemical reactions—specific and nonspecific reactions—and especially the reactions within the cell, or macroreactions for describing the organism-specific metabolic networks (MNs), which consist of substrates, metabolites (also called nodes of the metabolic network), products and the biochemical reactions between them. These biochemical reactions are defined in terms of their:

(a) stoichiometry,
(b) reversibility (under biological conditions),
(c) integration in a stoichiometric network.

Until now, the measured data have mainly been used for qualitative monitoring of the process. What will now be presented is a selection of technical problems which require dynamic process models to solve them.

One technical use of the process know-how in the sense of the application yields model-based estimation of the state of a process in a bioreactor. Methods such as the "extended Kalman Filter" allow a continuous estimation of process quantities, concerning which there are measurements in a discontinuous manner [Welch G, Bishop G. 1995. An Introduction to the Kalman Filter. Chapel Hill, N.C., USA: University of North Carolina at Chapel Hill.]. The course of non-measurable quantities, too, can be calculated from other measurements. This requires a process model which correctly describes the underlying process.

A further use is model-based, optimal process control. This uses a dynamic process model in order to optimize process control with respect to amount of product, product features or formation of by-products or other target quantities in a model-based, predictive closed-loop control circuit. For example, this is demonstrated by Frahm et al. for a hybridoma cell culture [Frahm B, Lane P, Atzert H, Munack A, Hoffmann M, Hass V C, Portner R. 2002. Adaptive, Model-Based Control by the Open-Loop-Feedback-Optimal (OLFO) Controller for the Effective Fed-Batch Cultivation of Hybridoma Cells. Biotechnol. Prog. 18(5): 1095-1103].

In the case of the two aforementioned technical uses, it is important for the process model created to have as low a complexity as possible, i.e. a limited number of state variables and/or equations, and at the same time good accuracy in the reproduction of the process.

In addition to the aforementioned uses in relation to process control, dynamic process models can also be used during process development in order to design experiments with optimal information acquisition. This approach is referred to as model-based design of experiments [Franceschini G, Macchietto S. 2008. Model-based design of experiments for parameter precision: State of the art. Chemical Engineering Science 63(19):4846-4872]. In addition to the above-mentioned prerequisites for the complexity of the model, said technical use requires a dynamic process model to be already present during the development phase. This should be able to be created as rapidly as possible from already existing process know-how in order to minimize the time taken for process development.

There was therefore a need to provide a method that allows the creation of a dynamic process model using background knowledge and process know-how. In order to be able to use this model for example for state estimation, optimal process control or in relation to model-based design of experiments, it is necessary for the complexity of the model to be low. Dependencies, i.e. influences of process quantities or of the process state on process behaviour, should be sufficiently accurately quantified within the design space. All available information about the process state should be used for this purpose. It should be possible to integrate the model-based description of product features into the model if required. The area in which process know-how is present is referred to as design space. The method should be applicable to the above-cited bioreactions and substantially shorten the development time of such dynamic models. Approaches to date for developing dynamic models require months to years until the completion of a process model. According to experience, the present approach reduces the development time to a few weeks.

Typical product features in the sense of the application are for example glycosylation patterns of proteins or protein integrity, but are not limited to these. To date, dynamic models used in the above-mentioned context do not have this property. The present approach allows a simple model-based integration of product features.

Model-based process control of fermentations is demonstrated by Frahm et al. for the example of a hybridoma cell culture (Frahm B, Lane P, Atzert H, Munack A, Hoffmann M, Hass V C, Portner R. 2002. Adaptive, Model-Based Control by the Open-Loop-Feedback-Optimal (OLFO) Controller for the Effective Fed-Batch Cultivation of Hybridoma Cells. Biotechnol. Prog. 18(5):1095-1103). Here, control of fundamental process quantities is model-based. There is no integration of product features. The mathematical model of the cell was devised for this specific process and can only be transferred with great effort to processes with the same organism or other organisms or strains of the same organism. Background knowledge in the form of reactions within the cell is not taken into account explicitly in the model. Integration of additional measured quantities into the model and thus complete utilization of information about the process state is only possible with considerable effort in this case. The approach therefore represents an individual solution, which is not transferable to other processes, and does not allow full utilization of the data obtained. The aforementioned method does not solve the above-mentioned technical problem owing to the model development time to be expected and the transferability of the solution to other processes with the same organisms or with other organisms, which involves effort.

More extensive modelling, which also incorporates product features such as glycosylation, can be found in the works of Kontoravdi et al. The model, which describes the principal metabolism, does not incorporate any background knowledge in the form of reactions within the cell, and also cannot be transferred to other processes with the same organism or other organisms. Additional measured quantities cannot be integrated into the model in this case [Kontoravdi C, Asprey S P, Pistikopoulos E N, Mantalaris A. 2007. Development of a dynamic model of monoclonal antibody production and glycosylation for product quality monitoring. Computers & Chemical Engineering 31(5-6): 392-400.]. This method also does not allow complete utilization of information about the process state, requires a long model development time and is not transferable to other organisms or strains. Therefore, this method is not a solution to the technical problem.

The models of glycosylation with integration of nucleotide sugar metabolism of Jedrzejewski et al. and Jimenez et al. incorporate background knowledge in the form of balance equations of internal metabolic intermediates [Jedrzejewski PM, del Val, Ioscani Jimenez, Constantinou A, Dell A, Haslam S M, Polizzi K M, Kontoravdi C. 2014. Towards Controlling the Glycoform: A Model Framework Linking Extracellular Metabolites to Antibody Glycosylation. International journal of molecular sciences 15(3):4492-4522; Jimenez del Val, Ioscani, Nagy J M, Kontoravdi C. 2011. A dynamic mathematical model for monoclonal antibody N-linked glycosylation and nucleotide sugar donor transport within a maturing Golgi apparatus. Biotechnology progress 27(6):1730-1743]. However, when using this model for process control, the complexity of the whole model and inadequate observability of metabolic intermediates within the cell are disadvantages. Moreover, the model of the principal metabolism does not allow transfer to other processes or the complete utilization of information about the process state. Therefore, this method is not a solution to the technical problem.

Flexible generation of models for bioprocesses is addressed by Leifheit et al. [Leifheit J, Heine T, Kawohl M, King R. 2007. Rechnergestutzte halbautomatische Modellierung biotechnologischer Prozesse [Computer-aided semi-automatic modelling of biotechnology processes]. at—Automatisierungstechnik 55(5)]. The model is generated with the aid of process know-how, but without background knowledge. The procedure can be used for various processes with the same organism or other organisms. It is based on macroreactions, which are specified by the user himself. Their precise stoichiometries are determined in the method. The method is described for a small number of state quantities or measured quantities. Integration of additional state quantities or measured quantities would involve a significant increase in complexity of the method. If comprehensive data principles are used, such as are provided for example by the BaychroMAT® platform, this method would no longer be feasible. The method does not allow integration of product features. Therefore, it is not a solution to the above-mentioned technical problem.

The use of background knowledge in the form of macroreactions, which are obtained as elementary modes (EM) from the known metabolic (stoichiometric) networks of an organism, is described by Provost [Provost A. 2006. Metabolic design of dynamic bioreaction models. Faculté des Sciences Appliquées, Université catholique de Louvain, Louvain-la-Neuve, Louvain-la-Neuve, p. 81 ff., p. 107 ff. p. 118 ff.]. This method can be used for various organisms or strains of the same organism. The macroreactions for the process model are selected using process know-how. However, process segments are defined for which a predefined number of macroreactions are selected separately, at random. The method described provides in this case one of many possible combinations of elementary modes. The number of macroreactions, and therefore the complexity of the model, is fixed and cannot be altered. The method produces separate models for each process segment. Selection of the kinetics of the individual macroreactions takes into account the stoichiometry of the macroreactions selected. The kinetic parameters (model parameters) are not, however, adjusted to the process data. Instead, the use of separate process segment models generates the changes in the process data. Random selection of the reactions can indeed also be based on a comprehensive database, but the approach described for selection of the kinetics and the selected kinetics cannot represent the course of the process or the behaviour of the organism in the process. Furthermore, the use of several process segment models leads to an unnecessary increase in complexity of the process model. The dependencies, i.e. influences of process quantities or of the process state on process behaviour, are not quantified with this method. Once again, there is no integration of product features. Therefore, this method is not a solution to the above-mentioned technical problem.

There was therefore a need to provide a method that allows the rapid and efficient provision of a model based on process know-how and measured data and the optimization of product turnover and of critical product features taking background knowledge into account, and that does not have the aforementioned disadvantages.

The object was achieved by a method for creating a model of a bioreaction with an organism in a bioreactor, described as follows.

The application provides a computer-implemented method for creating a model of a bioreaction—especially fermentation or whole-cell catalysis—with an organism, which comprises the following steps:

a. Selected metabolic pathways of the organism, their properties of stoichiometry and reversibility are incorporated in the method as background knowledge. In other words one or more metabolic networks of the organism are incorporated in the method. Elementary modes (EMs) are calculated from this input.

b. The EMs are combined in a matrix K, wherein the EMs combine the metabolic pathways from a) in macroreactions. This matrix K thus contains the stoichiometry and reversibility properties of all possible macroreactions from the background knowledge.

c. The measured data (also called process know-how) concerning the bioreaction with the organism are entered.

d. Using an interpolation method, the specific rates for the organism—rates of secretion and uptake of one or more input quantities and output quantities—of the entered metabolic pathways are calculated on the basis of the measured data entered from c). Preferably, growth rates, especially preferably also death rates, of the organism are also calculated.

e. Relevant macroreactions are selected in the form of a subset of the elementary modes from b) by i. data-independent and/or data-dependent prereduction of the number of EMs from b).
ii. selection of the subset from the prereduction from e)
   i. using the measured data from c) and/or one or more rates from d), preferably using the measured data from c), by means of an algorithm according to a mathematical quality criterion and combination of the subset in a matrix L.
   iii. Optionally, the subset is shown graphically.
f. Using an interpolation method, the reaction rates of the macroreactions of the subset r(t) are calculated on the basis of the input measured data from c) and/or the rates from d).
g. Kinetics of the macroreactions of the subset from e) ii. are devised using the following intermediate steps; the model parameters are defined thereby.
   i. Generic kinetics are devised from the stoichiometry of the macroreactions.
   ii. Quantities influencing the macroreactions are determined from the reaction rates from f).
   iii. The generic kinetics from g) i. are expanded by terms which quantify the influencing quantities determined in g)
h. Optionally, for the kinetics from g), a first adjustment of the values of the model parameters to the calculated reaction rates from f) is performed separately for each macroreaction and the quality of adjustment is checked.
i. Optionally, steps g) and h) are repeated until a predefined quality of adjustment is reached.
j. The values of the model parameters are adjusted to the measured data from c).
k. The matrix L, the kinetics from g) and the values of the model parameters from j) form the model and are presented as the output and/or transferred to a process control module or process development module.

Typically, the process control module communicates online with a distributed control system, which is customarily used for controlling the bioreactor.

Typically, process development modules are used for off-line optimization of the process or for designing experiments.

The bioreaction modelling according to the invention is based essentially on the assumption of representative macroreactions, which are a simplified representation of internal metabolic processes. Selection of the reactions requires both biochemical background knowledge, and process know-how.

In the first step of the method, the reactions of the metabolic network, their stoichiometry and reversibility property are input by the user via a user interface or ideally automatically by selecting an organism and its deposited metabolic pathways from a database module, in which the background knowledge about the organism is stored. The metabolic network (also called stoichiometric network in the prior art) and the properties of its individual reactions represent the background knowledge of the organism. Preferably, the metabolic network contains reactions from metabolic pathways important to the organism, for example glycolysis reactions. Especially preferably, the selection contains external reactions. An external reaction in the sense of the application contains at least one component outside of the cell, typically at least one input quantity and/or at least one output quantity (product, by-product, etc.). Especially preferably, the metabolic network contains reactions that describe cell growth, e.g. in the form of a simplified reaction of internal metabolites to the external biomass. Without being limited to this, FIG. 5 and Table 1 in the example describe an applicable metabolic network.

Then elementary modes are calculated from the input metabolic pathways of the organism, combined in one or more stoichiometric networks. Each elementary mode is a linear combination of reaction rates from the metabolic pathways—i.e. internal and external reactions of the metabolic network, wherein both the "steady state" condition is fulfilled for internal metabolites and the reversibility or irreversibility of reactions is taken into account. With linear combinations of reactions that take into account the "steady state" condition for internal metabolites, no internal metabolites can accumulate.

An internal reaction in the sense of the application takes place exclusively within the cell.

Through externalization of an internal component, i.e. by classifying an actually internal component as input quantity or output quantity, it is possible to model the internal reaction connected with the externalized internal component as an external reaction and therefore avoid the "steady-state" condition for internal metabolites in this case.

A macroreaction in the sense of the application groups together all reactions that lead from one or more input quantities to one or more output quantities. Each elementary mode therefore describes a macroreaction. Compared to the method of Leifheit et al., in the sense of the application the macroreactions are determined on the basis of the background knowledge entered.

The elementary modes (EMs) are combined in a matrix E, preferably in a module for matrix construction, which is configured with a corresponding algorithm. Known algorithms can be used for constructing the elementary modes matrix. METATOOL may be mentioned as an example, without being limited to this: [Pfeiffer T, Montero F, Schuster S. 1999. METATOOL: for studying metabolic networks. Bioinformatics 15(3):251-257.]

With METATOOL, a first matrix E, which describes the entered internal and external reactions, is produced.

In step b), the (external) stoichiometric matrix $N_p$ is used to produce from matrix (E) a matrix consisting of possible macroreactions K.

$$K = N_p \cdot E \quad \text{(Formula 1)}$$

The transformation of matrix E to K is known from Provost [Provost A. 2006. Metabolic design of dynamic bioreaction models. Faculté des Sciences Appliquées, Université catholique de Louvain, Louvain-la-Neuve, Louvain-la-Neuve, p. 81].

The column vectors of matrix K describe the macroreactions. The row vectors describe the components of the macroreactions (input and output quantities). The stoichiometry of the macroreactions is entered into matrix K.

Each reaction rate that is possible in the sense of the metabolic network can be represented as a positive linear combination of these macroreactions.

The use of EMs as the basis of a process model is known in the prior art (e.g. from Provost A. 2006. Metabolic design of dynamic bioreaction models. Faculté des Sciences Appliquées, Université catholique de Louvain, Louvain-la-Neuve, Louvain-la-Neuve, p. 87, p. 118 ff. and Gao, J. et al. (2007). Dynamic metabolic modeling for a MAB bioprocess. *Biotechnology progress,* 23(1), 168-181).

In a further step c), the available measured data (process know-how) for the bioreaction with the organism are input. Typically, cell count, cell viability, concentrations of substrates, such as carbon sources (e.g. glucose), amino acids or $O_2$, products and by-products (e.g. lactate or $CO_2$), process parameters such as temperature and/or pH or product features are determined. This input can be manual by the user or automatic, for example by selecting from a database module for storage of measured data and transferring the selected data into a data analysis module, which is connected to the database module.

From these measured data, the cell-specific rates of secretion and uptake of substrates and (by-)products—together called specific rates q(t)—and optionally the growth and death rates of the organism ($\mu(t)$, $\mu_d(t)$) are calculated in step d). The calculation requires the interpolation of the viable cell count, the total cell count and media concentrations using an interpolation method. Temporal variations of the measured quantities can be determined therefrom. The calculated rates q(t), $\mu(t)$, $\mu_d(t)$ provide information about the observable dynamic behaviour of the organism over time.

For calculating the above-mentioned rates, one or more different interpolation method(s) can be used in combination.

As an example, Leifheit et al. describe determination of the temporal variations of measured quantities—e.g. those of the total cell count, those of the viable cell count, or those of other media concentrations—from measured data by means of spline-interpolated measured data [Leifheit, J., Heine, T., Kawohl, M., & King, R. (2007). Rechnergestutzte halbautomatische Modellierung biotechnologischer Prozesse [Computer-aided semi-automatic modelling of biotechnology processes]. at—*Automatisierungstechnik*, 55(5), 211-218]. This method is hereby incorporated in the application by reference.

The above-mentioned rates q(t), $\mu(t)$, $\mu_d(t)$ are calculated from these temporal variations: For example, it is possible to calculate the growth rate of the organism $\mu(t)$ from spline-interpolated values of the total cell count $X_t(t)$ and of the viable cell count $X_v(t)$ and from the temporal variation of the total cell count calculable therefrom $$\frac{dX_t}{dt}(t),$$

using Formula 2:

$$\frac{dX_t}{dt}(t) = -D(t) \cdot X_t(t) + \mu(t) \cdot X_v(t) \quad \text{(Formula 2)}$$

where D(t) is the dilution rate.

The death rate $\mu_d(t)$ can be calculated, when the course of $\mu(t)$ is known, from the course of $X_v(t)$ and the course of the temporal variation of the viable cell count $$\frac{dX_v}{dt}(t)$$

using Formula 3:

$$\frac{dX_v}{dt}(t) = -D(t) \cdot X_v(t) + (\mu(t) - \mu_d(t)) \cdot X_v(t) \quad \text{(Formula 3)}$$

The specific rates of another component i $q_i(t)$ can be calculated from spline-interpolated values of the viable cell count $X_v(t)$ and of the concentration of the component $C_i(t)$ and from the course of the temporal variation $$\frac{dC_i}{dt}(t),$$

which can be determined from spline-interpolated values of $C_i(t)$, using Formula 4:

$$\frac{dC_i}{dt}(t) = D(t) \cdot (C_{i,in} - C_i(t)) + q_i(t) \cdot X_v(t) \quad \text{(Formula 4)}$$

In a preferred embodiment of the method, the measured data from step c) are prepared as follows before the first interpolation: In order to take into account all concentration changes not caused by the cells and obtain a continuous course of the concentration changes from the measured data, the measured data are displaced (called "shifted" in the application). The amount $\Delta C_i(t)$ by which the concentration measurement is displaced can be calculated according to Formula 5:

$$\Delta C_i(t) = \int_0^t D(\tau) \cdot (C_i(T) - C_{i,in}(\tau)) d\tau \quad \text{(Formula 5)}$$

where $D(\tau)$ is the dilution rate. The shifted concentration course $C_{i,s}(t)$ is then yielded according to Formula 6:

$$C_{i,s}(t) = C_i(t) - \Delta C_i(t) \quad \text{(Formula 6)}$$

The differential equation specifying the course of the shifted concentration $C_{i,s}(t)$ is therefore yielded from Formulas 4 and 6 giving:

$$\frac{dC_{i,s}}{dt} = \frac{d(C_i(t) - \Delta C_i(t))}{dt} = q_i(t) \cdot X_v(t) \quad \text{(Formula 7)}$$

This preparation (shifting) of the measured data prevents a sudden change of the calculated specific rates when feed is started or stopped (feed peak), especially in a fed-batch process.

FIG. 1 shows the preparation/shifting of the measured data in the sense of this application.

In a special embodiment of the method, the prepared data are then used for calculating a gradient of the total cell count $$\left.\frac{dX_t}{dt}\right|_s (t)$$

with the method of Leitheit et al. This is approximated with a spline-interpolation according to differential equation 8:

$$\left.\frac{dX_t}{dt}\right|_s (t) = \mu(t) \cdot X_v(t) \quad \text{(Formula 8)}$$

Especially preferably, lysis is included in the calculation with a lysis factor $K_l$ (Formula 9). This can for example be assumed to be constant over the course of the process.

$$\left.\frac{dX_t}{dt}\right|_s \mu(t) \cdot X_v(t) - K_l \cdot (X_t(t) - X_v(t)) \quad \text{(Formula 9)}$$

The drop in the shifted total cell count $X_{t,s}(t)$ can thus be explained by lysis, so that negative values for the growth rate $\mu(t)$ can be avoided.

Preferably, the prepared data are also used for calculating the death rate $\mu_d(t)$.

Preferably, the possible combinations of specific rates $q(t)$ are presented in a flux-map diagram, for example as in FIG. 2. This manner of presentation provides a good overview of the calculated specific rates $q(t)$. The contour lines indicate here which regions are physiologically important.

If the specific rates $q(t)$ and optionally the further rates $\mu(t)$ and $\mu_d(t)$ have different orders of magnitude and units, these are usually combined by means of simplifications into a specific rate vector $\tilde{q}(t)$ with the same units. For example, the specific rate of a macromolecule that is measured in grams [g] will have the unit $$\left[\frac{g}{\text{Cell} \cdot h}\right].$$

If the composition of this macromolecule is estimated, e.g. based on its C-mol content, its specific rate can be represented altered from [g] to [C-mol], so that the specific rate has the unit $$\left[\frac{C-\text{mol}}{\text{Cell} \cdot h}\right].$$

The specific rates $\tilde{q}(t)$ form one of the bases for the next step e) of the method, namely selection of the relevant macroreactions.

In step e), a subset (L) of the EMs is selected on the basis of the data, and this can represent well the specific rates $\tilde{q}(t)$ from d) and/or the measured data from c) according to a mathematical quality criterion. The number of EMs in the subset (L) should be as small as possible in order to ensure as low a complexity of the process model as possible. However, the subset L should ensure a good description of the process know-how.

Selection of EMs reduces the size of the solution space compared to the original set of EMs (K) from a), but in addition contains the physiologically important region of the cells that has been determined. FIG. 3 shows a representation of the solution space, where the original set of EMs (K) is reduced to a subset (L).

For step e), the calculated specific rates $\tilde{q}(t)$ and the measured data from c) are usually transferred to a module for selecting the relevant macroreactions, which is configured with corresponding algorithms. In step e) i., a data-independent and/or a data-dependent prereduction of matrix K is done in any desired order:

The data-independent prereduction is preferably done by means of a geometric reduction. This involves calculating all cosine similarities to all other modes for a randomly selected EM. The EM with the highest similarity is removed from the set. This procedure is repeated until a predefined number of EMs is reached. The desired number is usually defined beforehand for the method. The volume of the solution space can be used as a control variable. It was found that, surprisingly, a distinct reduction in the number of macroreactions while maintaining 90 to 98%, preferably 92 to 95%, of the spanned volume compared to the original volume is possible.

The data-dependent prereduction can be done by comparing yield coefficients of the EMs ($Y^{EM}$) with the yield coefficients calculated from the specific rates $\tilde{q}(t)$ from d) ($Y^m$). The yield coefficient of the k-th EM ($Y_{i,j}^{EM,k}$) is determined according to Formula 10 by dividing the corresponding stoichiometric coefficients of the external metabolites i and j. For the k-th EM, these are the matrix entries $K_{i,k}$ and $K_{j,k}$.

$$Y_{i,j}^{EM,k} = \frac{K_{i,k}}{K_{j,k}} \quad \text{(Formula 10)}$$

If the stoichiometric coefficient $K_{j,k}=0$, the yield coefficient cannot be determined.

The yield coefficient $Y_{i,j}^m(t)$ indicates, according to Formula 11, the ratio between two cell-specific rates that have been measured or calculated according to d) ($\tilde{q}_i(t),\tilde{q}_j(t)$):

$$Y_{i,j}^m(t) = \frac{\tilde{q}_i(t)}{\tilde{q}_j(t)} \quad \text{(Formula 11)}$$

From the yield coefficients $Y^m$, it is possible to determine an upper and a lower limit for each possible combination of two external components i and j. For example, it is possible to use the smallest yield coefficient of two external metabolites i and j $Y_{i,j}^m(t)$ as lower limit and the largest value of $Y_{i,j}^m(t)$ as upper limit, though other limits are also possible. EMs which have yield coefficients $Y_{i,j}^{EM}$ above the upper limit or below the lower limit are removed from matrix K. If the yield coefficient of an EM $Y_{i,j}^{EM}$ cannot be determined, it remains in matrix K. Preferably, it is also possible to use the inventive method "linear estimation of reaction rates of selected macroreactions with NNLS", as described on page 15, for the data-dependent prereduction. The method in the context of prereduction is explained there. The advantage of using the process data in the data-dependent prereduction in the method is that the reduction is process-related and thus more effective and focussed.

In step e) ii., a subset of macroreactions is selected using an algorithm: Selection requires a quality criterion, which makes it possible to quantify how well the specific rates $\tilde{q}(t)$ from d) and/or the measured data from c) can be represented with a subset (L), and also an algorithm for selecting the subset.

The quality criterion used for representing calculated specific rates $\tilde{q}(t)$ with a subset L can be, according to Soons et al., the sum of squared residuals of the specific rates ($SSR_q$) according to Formula 12 [Soons, Z. I. T. A., Ferreira, E. C., Rocha, I. (2010). Selection of Elementary Modes for Bioprocess Control. 11th International Symposium on Computer Applications in Biotechnology, Leuven, Belgium, 7-9 Jul. 2010, 156-161].

$$SSR_q = \sum_{i=1}^{N_t} \|L \cdot r(t_i) - \tilde{q}(t_i)\| \quad \text{(Formula 12)}$$

The value for $SSR_q$ should be as small as possible.

Minimizing $SSR_q$ requires determining beforehand for each considered time point $t_i$ the vector $r(t_i)$ with the aid of a non-negative least squares algorithm, such that:

$$\min_{\underline{r}(t_i)}(\|L \cdot \underline{r}(t_i) - \underline{\tilde{q}}(t_i)\|) \quad \text{(Formula 13)}$$

with the additional boundary condition:

$$\underline{r}(t_i) \geq 0 \quad \text{(Formula 14)}$$

The advantage of this method is that the calculations according to Formulas 12-14 can even be carried out for very large subsets with many EMs. A significant disadvantage is that this calculation requires the calculated specific rates $\underline{\tilde{q}}(t)$. Since they are obtained from interpolated measured values, they are associated with great uncertainty with regard to their true values. In some circumstances, measurement inaccuracies may have a very large impact on the calculated specific rates $\underline{\tilde{q}}(t)$. Consequently, the quality criterion $SSR_q$ may also be determined only with great uncertainty. In addition to the information about representation quality, this method also yields an estimated course of the reaction rates $\underline{r}(t)$ of the subset L as the result of the minimization according to Formulas 13 and 14.

Leighty, R. et al. describe another method in which the measured values (concentration measurements) are approximated directly by a linear estimation of volumetric reaction rates over time. By solving a linear optimization problem with a linear least squares solver, the course of the reactions can be estimated quickly, assuming that it proceeds linearly between supporting points [Leighty, R. W., & Antoniewicz, M. R. (2011), Dynamic metabolic flux analysis (DMFA): a framework for determining fluxes at metabolic non-steady state. *Metabolic engineering*, 13(6), 745-755]. This method only relates to reversible macroreactions (such as the "free fluxes" mentioned in the source), moreover, dilution effects (hence concentration changes that are not caused by the cells) cannot be taken into account. If the dimensions of the macroreactions and of the measured values do not agree, these measured values cannot be used for estimating reaction rates. This is for example the case when cell growth in the form of formation of external biomass is part of the macroreactions and only the cell dry mass is known from the measured values. In this form, therefore, this method is not suitable for the use of irreversible macroreactions and fed-batch processes.

Employing the concept of Leighty et al., which is hereby incorporated in this application by reference, with the data prepared (shifted) according to the invention, this method can now also be applied to fed-batch processes. Furthermore, by adding a lower limit for the reaction rates of the macroreactions as a boundary condition of the linear optimization problem, the method can also be used for irreversible reactions—like the elementary modes. If the dimensions of the macroreactions and of the measured values are not in agreement, by means of suitable correlations the dimension of the measured values can be adjusted to that of the macroreactions. This combination of the linear estimation according to Leighty et al. with the improvements from this application is designated in the following as "linear estimation of reaction rates of selected macroreactions".

It is thus possible to verify whether the measured data can be adequately represented with the selected macroreactions of a subset L of the original EM-set K. The final sum of squared residuals $SSR_C$ according to Formula 15 between the shifted concentrations determined with the method $\hat{\underline{C}}_s(t)$ and the shifted concentrations $\underline{C}_s(t)$, as calculated here, indicates how well the measured data can be represented with the subset.

$$SSR_C = \sum_{i=1}^{N_t} \sum_{j=1}^{N_c} (C_{j,s}(t_i) - \hat{C}_{j,s}(t_i))^2 \quad \text{(Formula 15)}$$

The smaller the value of $SSR_C$, the better the subset L. This method is especially preferred for modelling fed-batch processes, over the method by Soons et al., as rapid verification of the quality of a subset is possible even without a possibly erroneous prior determination of the specific rates. Assuming that the estimated reaction rates proceed linearly between supporting points, measurement deviations have very little impact on the estimation of the reaction rates. The disadvantage of this method is that the size of the subset L under examination is limited by the solution to the linear optimization problem. The maximum number of reactions in the subset is equal to the number of available measurements divided by the number of supporting points.

In addition to the information about representation quality, this method also yields an estimated course of the reaction rates of the subset $\underline{r}(t)$.

In a preferred embodiment of the inventive "linear estimation of reaction rates of selected macroreactions", the linear optimization problem is solved by using, instead of a linear least squares solver, the non-negative least squares solver (NNLS) by Lawson et al. [Lawson, C. L. and R. J. Hanson, Solving Least Squares Problems, Prentice-Hall, 1974, Chapter 23, p. 161.]. This makes it possible to verify too the quality of larger subsets with the method. In this case, the maximum number of macroreactions can also be significantly greater than the number of available measurements divided by the number of supporting points. This combination of the "linear estimation of reaction rates of selected macroreactions" with the use of the non-negative least squares solver is designated in the following as "linear estimation of reaction rates of selected macroreactions with NNLS".

The inventive method of "linear estimation of reaction rates of selected macroreactions with NNLS" can be additionally used as a further data-dependent method in relation to prereduction of the EMs in step e) i). For this purpose, it is possible to use here a very large set K of macroreactions. The result of the method is, firstly, the value for $SSR_C$ and, secondly, the course of the reaction rates $\underline{r}(t)$. EMs with small values of the associated rate $\underline{r}(t)$ are removed from matrix K. This procedure is repeated until a predefined number of EMs is reached or the value of $SSR_C$ exceeds a specified threshold.

Algorithms for selecting the subset are known e.g. from Provost et al. and Soons et al. [Provost A. 2006. Metabolic design of dynamic bioreaction models. Faculté des Sciences Appliquées, Université catholique de Louvain, Louvain-la-Neuve, Louvain-la-Neuve; Soons, Z. I. T. A., Ferreira, E. C., & Rocha, I. (2010). Selection of elementary modes for bioprocess control.]. 11th International Symposium on Computer Applications in Biotechnology, Leuven, Belgium, 7-9 Jul. 2010, 156-161].

Soons et al. describe the formation of an EM-subset in a two-stage optimization method. In the case of various, randomly selected EMs, the values for $SSR_q$ are minimized in each case as described above. The set with the smallest minimized $SSR_q$ value is selected. With a large number of EMs, however, random selection is ineffective, as there is a very marked increase in the number of possible combinations. For example, when selecting 10 reactions from a set of 20 000 EMs, there are more than $2.8 \cdot 10^{36}$ combinations.

The probability of finding the optimum combination is then very slight. Owing to the use of the quality criterion $SSR_q$, this method is vulnerable to measurement uncertainties and measurement deviations.

Provost describes an alternative algorithm in which all possible positive linear combinations of elementary modes are determined for various specific values of $\underline{\tilde{q}}(t_i)$ i=1, ..., n, where: $SSR_q(t=t_i)$=0. Then a combination is selected at random from these numerous possible combinations. In each case this method uses only one vector $\underline{\tilde{q}}(t_i)$ and not the entire variation over time. Therefore selection of EMs for the complete process is not possible. With random selection, the vector $\underline{\tilde{q}}(t_i)$ may indeed be represented, but the extent to which the rest of the process can be represented hereby is not determined. Another disadvantage of this method is that a vector $\underline{\tilde{q}}(t_i)$ that does not lie within the solution space of all EMs cannot be used. An approximate solution cannot be determined. This is a great disadvantage particularly in the case of uncertain measurements and specific rates. Owing to the use of the quality criterion $SSR_q$, this method is likewise vulnerable to measurement uncertainties and measurement deviations.

In a preferred further embodiment of the method, an evolutionary, especially genetic, algorithm is therefore used for selecting the relevant macroreactions, i.e. for selecting the EM-subset L. Such an algorithm is known for example from Baker et al. [Syed Murtuza Baker, Kai Schallau, Björn H. Junker. 2010. Comparison of different algorithms for simultaneous estimation of multiple parameters in kinetic metabolic models. J. Integrative Bioinformatics:-1-1.]. Especially preferably, it is possible to use a genetic algorithm, in the target function of which the method "linear estimation of reaction rates of selected macroreactions" is used to calculate the corresponding value $SSR_C$ for various combinations of EMs. Alternatively, random selection may also be used. After completion of step ii), the matrix L contains the necessary macroreactions (step iii).

In an optional step iii), the validity of the EM-subset L is verified graphically. In this case, it is possible to use the flux map from step d) as projection of the EM-subset L. FIG. 4 shows the flux map with the projection of a subset of six EMs. If the EM-subset L is valid, the measured data are still located within the EM-subset L. This representation allows a rapid graphic check of the validity of selection.

In a further step f), the specific rates $\underline{\tilde{q}}(t)$ from d) and/or the measured data from c) are used to calculate the reaction rates of the macroreactions of the subset L. The calculation of $\underline{r}(t)$ can be done according to Soons et al. on the basis of the specific rates $\underline{\tilde{q}}(t)$ as described in e) [Soons, Z. I. T. A., Ferreira, E. C., Rocha, I. (2010). Selection of Elementary Modes for Bioprocess Control. 11th International Symposium on Computer Applications in Biotechnology, Leuven, Belgium, 7-9 Jul. 2010, 156-161]; preferably, the calculation of $\underline{r}(t)$ is done on the basis of the measured data from c) using the inventive "linear estimation of reaction rates of selected macroreactions".

In step g) of the method, the kinetics of the macroreactions are devised. The kinetics determined should quantify the dynamic influences of the process state on the respective reaction rates $\hat{r}_k$:

$$\hat{r}_k = f(\underline{C}, pH, T, \ldots) \qquad \text{(Formula 16)}$$

The model parameters to be determined are found from the kinetics.

In step g) i., the generic kinetics are devised from the stoichiometry of the macroreactions. For substrates of the macroreaction i, a limitation of the Monod type is assumed. The maximum reaction rate is multiplied by the various limitations $\tilde{r}_i$:

$$\hat{r}_k(t) = r_{k,max} \cdot \prod_{i=1}^{N_l} \tilde{r}_i(t) = r_{k,max} \cdot \prod_{i=1}^{N_l} \left( \frac{C_i(t)}{K_{m,k,i} + C_i(t)} \right)^{n_i} \qquad \text{(Formula 17)}$$

where the Monod constants $K_{m,k,i}$ and the Hill coefficients $n_i$ are the parameters of the equation, the first values of which are entered manually. Usually, the Monod constants $K_{m,k,i}$ are set to a tenth of the respective maximum measured concentrations and the Hill coefficients $n_i$ are set to a value of 1. Determination of generic kinetics from the reaction stoichiometries is described by Provost or by Gao et al. [Provost A. 2006. Metabolic design of dynamic bioreaction models. Faculté des Sciences Appliquées, Université catholique de Louvain, Louvain-la-Neuve, P/. 126; [Gao, J., Gorenflo, V. M., Scharer, J. M., & Budman, H. M. (2007). Dynamic metabolic modeling for a MAB bioprocess. *Biotechnology progress*, 23(1), 168-181]. These methods are hereby incorporated in the application by reference. These methods employ the substrate limitations of the Monod type for the respective substrates of a reaction. Although this is not described by Provost or Gao, inhibitions due to toxic products can also be derived from the reaction stoichiometry using this method.

In step g) ii., the quantities influencing the reaction rates $\underline{r}(t)$ determined in f) are determined. This involves considering all quantities which describe the process state (i.e. including bioreaction conditions, for example pH, reactor temperature, partial pressures, which are not derivable from the stoichiometry of the macroreaction). The influencing quantities can be determined manually, for example with the aid of a statistical method such as partial least squares. To this end, the correlation between the process state (which is combined in a matrix) and the reaction rates $\underline{r}(t)$ from f) is determined.

In a step g) iii., the influences determined in g) ii. are then quantified and the kinetics from i. are expanded by corresponding terms. An influence of a quantity of the process state on a reaction rate, as found in g) can then be provided with a term $\tilde{r}_i$. The term $\tilde{r}_i$ is any desired function which, depending on the process state, yields a value between 0 and 1. The generic kinetics of the reaction, as established in g) i., is then multiplied by this term.

For example, if a negative correlation is found between the concentration of a component i and the reaction k, this indicates influencing of the reaction rate k by the concentration of i ($C_i$). This can for example be provided with inhibition kinetics according to Haldane:

$$\tilde{r}_i(t) = \frac{K_{I,k,i}}{K_{I,k,i} + C_i(t)} \qquad \text{(Formula 18)}$$

where $K_{I,k,i}$ denotes the inhibition constant and is a further model parameter, the first value of which is entered manually and is usually set to a tenth of the respective maximum measured concentrations.

In an optional step h), the values of the model parameters $\underline{p}$ of the kinetics are adjusted to the reaction rates of the macroreactions $\underline{r}(t)$ determined in f):

$$\min_{\underline{p}} \sum_{k=1}^{N_t} (\hat{r}_k(\underline{p}) - r_k)^2 \qquad \text{(Formula 19)}$$

This is designated in the following as model parameter value estimation. Numerical solution of one or more differential equations according to Formulas 2 to 4 may be omitted in this step; in independent groups with usually 3 to 10 parameters, the values of the model parameters can be adjusted separately for each macroreaction k. Adjustment is done by a customary method such as the Gauss-Newton method [Bates DM, Watts DG. 1988. Nonlinear regression analysis and its applications. New York: Wiley. xiv, 365.].

This model parameter value estimation, separate for each macroreaction, is especially advantageous for steps i) and j), because on the one hand it can be executed quickly, and on the other hand it provides improved starting values for adjusting the values of the model parameters to measured data from c) in step j).

The quality of adjustment is for example calculated using the sum of squared residuals $SSR_r$ according to Formula 20:

$$SSR_r = \sum_{k=1}^{N_t} (\hat{r}_k(\underline{p}) - r_k)^2 \qquad \text{(Formula 20)}$$

The smaller the value for $SSR_r$, the better the adjustment. Alternatively, the quality of adjustment is verified by a graphical comparison of $\hat{r}_k$ and $r_k$.

In an optional step i), the kinetics of the macroreactions selected in g) is checked for quality of adjustment. This is based on the value $SSR_r$ which is calculated in step h) and which quantifies the quality of adjustment of the model parameter value estimation. If the quality of adjustment is unsatisfactory, steps g) and h) may be repeated, until a predefined quality of adjustment is reached.

In a further step j), the parameter values of the kinetics from g) can be adjusted to the measured data from c) by a usual method for adjustments. The starting values from step h) are preferably used for this adjustment. The model parameter value adjustment takes place with incorporation of the above-mentioned differential equations (Formulas 2 to 4), e.g. by means of the Gauss-Newton method [Bates D M, Watts D G. 1988. Nonlinear regression analysis and its applications. New York: Wiley. xiv, 365.] or using a multiple-shooting algorithm [Peifer M, Timmer J. 2007. Parameter estimation in ordinary differential equations for biochemical processes using the method of multiple shooting. Systems Biology, IET 1(2):78-88].

Preferably, product features can be integrated into the model. Especially preferably, this can be introduced for product features that depend on the concentration of by-products or intermediates. Concentrations of by-products which are external components of the metabolic network entered in a) are already integrated into the model and can be calculated. If required, however, other by-products or intermediates can also be combined in one or more separate metabolic networks. This is advantageous if the expected secretion or uptake rates are of different orders of magnitude or specified metabolic processes are to be examined in different degrees of detail. As an alternative to an integrated model, with steps a) to j) it is possible to produce a separate model for calculating the product features, which describes the course of the process of the external components of the separate metabolic network, also with a set of macroreactions with their own kinetics. By-products or intermediates that are not located outside of the organism, but whose accumulation within the cell affects one or more product features, may be externalized in step a) and b) during calculation of the EMs and formulation of the macroreactions, and may thus be classified as external components. The integration of product features that are dependent on concentrations inside the cell or outside the cell may then take place by additional integration of quantitative or qualitative relationships between concentrations and product features.

The invention further provides a computer program or software for carrying out the method according to the invention.

The model provided using the method according to the invention can be used for process control or planning process control and investigation of the process in the reactor.

Without being limited thereto, a special embodiment of the method according to the invention will be described as an example. With this method, as an example, a model of fermentation with hybridoma cells was also prepared and its validity was tested as described.

Example: Modelling of a Hybridoma Cell Culture

1 Step a)

The background knowledge in the form of a metabolic network was taken from the work of Niu et al. (Metabolic pathway analysis and reduction for mammalian cell cultures—Towards macroscopic modeling. Chemical Engineering Science (2013) 102, pp. 461-473. DOI: 10.1016/j.ces.2013.07.034.). The metabolic network of an animal cell described here contains 35 reactions, which link together 37 internal and external metabolites (see FIG. 5; see Table 1).

TABLE 1

Reactions of the metabolic network according to Niu et al.
(Metabolic pathway analysis and reduction for mammalian cell
cultures - Towards macroscopic modeling. Chemical Engineering
Science (2013) 102, pp. 461-473. DOI: 10.1016/j.ces.2013.07.034.)

1 Glucose → 1 G6P
1 G6P + 2 NAD → 2 Pyruvate
1 Pyruvate → 1 Lactate + 1 NAD
1 Pyruvate → 1 Pyruvate_m
1 NADm + 1 Pyruvate_m → 1 Acetyl coA_m
1 Acetyl coA_m + 1 NADm + 1 Oxaloacetate_m → 1 α-ketoglutarate_m
1-ketoglutarate_m + 1 NADm → 1 Succinyl CoA_m
1 FADm + 1 Succinyl CoA_m → 1 Fumarate
1 Fumarate → 1 Malate_m TABLE 1-continued Reactions of the metabolic network according to Niu et al.
(Metabolic pathway analysis and reduction for mammalian cell
cultures - Towards macroscopic modeling. Chemical Engineering
Science (2013) 102, pp. 461-473. DOI: 10.1016/j.ces.2013.07.034.)

1 Malate_m + 1 NADm → 1 Oxaloacetate_m
1 Glutamine → 1 Glutamate + 1 NH3
1 Glutamate + 1 NADm → 1 α-ketoglutarate_m + 1 NH3
1 Malate_m → 1 Malate
1 Malate + 1 NAD → 1 Pyruvate
1 Glutamate + 1 Pyruvate → 1 α-ketoglutarate_m + 1 Alanine
1 Glutamate + 1 Oxaloacetate_m → 1 α-ketoglutarate_m + 1 Aspartate
1 Arginine + 2 NADm → 1 Glutamate + 3 NH3
1 Asparagine → 1 Aspartate + 1 NH3
2 Glycine + 1 NADm → 1 NH3
1 Histidine + 1 NADm →1 Glutamate + 2 NH3
1 Isoleucine + 2 NADm → 1 Acetyl coA_m + 1 NH3 + 1 Succinyl CoA_m
1 Leucine + 3 NADm → 3 Acetyl coA_m
1 Lysine + 6 NADm → 2 Acetyl coA_m
1 Methionine + 4 NADm → 1 NH3 + 1 Succinyl CoA_m
1 NADm + 1 Phenalanine → 1 Tyrosine
1 Serine → 1 NH3 + 1 Pyruvate
1 NADm + 1 Threonine→1 NH3 + 1 Succinyl CoA_m
19 NADm + 1 TRP → 3 Acetyl coA_m
5 NADm + 1 Tyrosine →2 Acetyl coA_m + 1 Fumarate
5 NADm + 1 Valine →1 NH3 + 1 Succinyl CoA_m
1 NADm →1 NAD
0.5 Oxygen(O2) →1 NADm
1 NADm →1 FADm
0.0156 Alanine + 0.0082 Arginine + 0.0287 Aspartate + 0.0167 G6P + 0.0245 Glutamine + 0.0039 Glutamate + 0.0196 Glycine + 0.0038 Histidine + 0.0099 Isoleucine + 0.0156 Leucine + 0.0119 Lysine + 0.0039 Methionine + 0.0065 Phenylalanine + 0.016 Serine + 0.0094 Threonine + 0.0047 Tyrosine + 0.0113 Valine →1 X (Biomass) + 0.0981 NAD
0.01101 Alanine + 0.005033 Arginine + 0.007235 Asparagine + 0.0081787 Aspartate + 0.010381 Glutamine + 0.010695 Glutamate + 0.01447 Glycine + 0.0034602 Histidine + 0.005033 Isoleucine + 0.014155 Leucine + 0.01447 Lysine + 0.0028311 Methionine + 0.007235 Phenylalanine + 0.026738 Serine + 0.016043 Threonine + 0.0084932 Tyrosine + 0.018874 Valine →1 IgG (Antibody)

Reversibility of the reactions is not explicitly stated in the published work. Instead, the data on "metabolic flux analysis" from the same publication were evaluated and were used for identifying the irreversible reactions.

With the stoichiometric matrix N, which contains the stoichiometry, i.e. the stoichiometric coefficients, of the internal metabolites, and the information about the reversibility of the reactions, all elementary modes (EMs) of the network were calculated using METATOOL 5.1 (Pfeiffer et al. METATOOL: for studying metabolic networks, Bioinformatics 199915 (3), pp. 251-257). The number of EMs is in this case over 300 000.

2 Step b)

The matrix with the calculated EMs E was obtained in step a) Similarly to matrix N, the matrix $N_p$ contains the stoichiometry, i.e. the stoichiometric coefficients, of the external metabolites. Possible macroreactions of the stoichiometric network were combined in matrix K with Formula 21:

$$K = N_p \cdot E \quad \text{(Formula 21)}$$

3 Step c)

The measured data of the process were taken from Baughman et al., which gives various measured quantities of a fermentation of hybridoma cells over the course of a batch process (cf. FIG. 6) [On the dynamic modeling of mammalian cell metabolism and mAb production. In: Computers & Chemical Engineering (2010) 34 (2), pp. 210-222]. The measured data were entered into the method.

4 Step d)

Using spline-interpolated measured values from c) ($\underline{C}^{int}$), the growth and death rates and the specific uptake and secretion rates were calculated (cf. FIG. 7). Lysis was incorporated with a predefined lysis factor $K_l=0.1$, which was entered into the method and was constant over the process time. Shifting of the measured data was not necessary, because in this case they are data of a batch process without further additions. Accordingly, the data show a rising course, because all concentration changes are caused by the cells, and not by additions.

Additional information is employed for calculating the rates $\tilde{q}$. Thus, with the aid of the total biomass (BM in $$\left[\frac{C\text{-mol}}{l}\right]\right),$$

also given in the data set from Baughman et al., and the total cell count, an average C-mol content of $$f_{C\text{-}mol,X_v} = 18.41 \left[\frac{C\text{-mol}}{10^9 \text{ cells}}\right]$$

could be calculated. The C-mol-based growth rate could now be calculated from Formula 22:

$$\tilde{\mu}\left[\frac{C\text{-mol}}{h \cdot 10^9 \text{ cells}}\right] = \mu\left[\frac{1}{h}\right] \cdot f_{C\text{-}mol,X_v}\left[\frac{C\text{-mol}}{10^9 \text{ cells}}\right] \quad \text{(Formula 22)}$$

The C-mol based rate of formation of the antibody can be estimated similarly. For this, the molar composition of the antibody was estimated as $CH_{1.58}O_{0.31}N_{0.27}S_{0.004}$ with a formal molar mass of $$M_{mAb,C\text{-}mol} = 22.45 \frac{g}{mol}.$$

Here, it is assumed that the molar composition corresponds to an average molar composition of proteins as indicated by Villadsen et al. [Bioreaction engineering principles (2011), Chapter 3, Elemental and Redox Balances, p. 73, Springer Verlag, ISBN: 978-1-4419-9687-9]. The molar mass of the whole antibody was estimated at $$M_{mAb} = 150,000 \frac{g}{mol}.$$

The rate of formation of the antibody was then obtained from the formula:

$$\tilde{q}_{mAb}\left[\frac{C\text{-}mol}{h \cdot 10^9 \text{cells}}\right] = q_{mAb}\left[\frac{10^{-4} mol}{h \cdot 10^9 \text{cells}}\right] \cdot \frac{M_{mAb,C\text{-}mol}}{M_{mAb}} \cdot 10^4 \quad \text{(Formula 23)}$$

The temporal variation of the rates $\tilde{q}(t)$ could then be employed for selecting the macroreactions.

5 Step e)

In step e), an EM-subset of macroreactions was produced, with which the data set was reproduced as well as possible. This required the matrix K from step b). As the number of over 300 000 macroreactions would have led to an excessively large number of possible combinations, a data-dependent prereduction was carried out first.

To this end, the rates $\tilde{q}(t)$ determined in step d) were used for calculating the yield coefficients $Y^m$ for all combinations of two external metabolites. The lower limit of a yield coefficient $Y_{i,j}$ was selected such that 99% of the determined yield coefficients $Y_{i,j}^m(t)$ are above this value. The upper limit was selected such that 99% of the determined yield coefficients $Y_{i,j}^m(t)$ are below this value. By way of example, Table 2 shows some determined limits and also the proportion of EMs having yield coefficients $Y_{i,j}^{EM}$ within these limits. Overall, the number of EMs could thus be reduced to approx. 3000.

TABLE 2

External metabolites, their maximum and minimum yield coefficients $Y_{i,j}$, and the proportion of EMs having yield coefficients within the specified limits

| External components | Lower limit | Upper limit | Proportion of EMs within the limits |
|---|---|---|---|
| Ala:Asn | −14.6811 | −0.1752 | 99.9134% |
| Asn:Glc | 0.0293 | 16.1603 | 64.0488% |
| Asp:Ala | −1.1130 | −2.1011 | 74.0839% |

After the data-dependent reduction, a data-independent reduction was subsequently additionally carried out. In this case, a maximum value for the cosine similarity of two EMs of 0.995 was defined. Beginning with the first reaction, all macroreactions that exceeded this value were thus removed from matrix K. There remained approx. 500 macroreactions from matrix K (also called reduced matrix K), which still cover more than 95% of the volume of the solution space spanned by the approx. 3000 EMs.

Before the selection process, a reconciliation of the components indicated in the metabolic network according to Niu et al. (which correspond to the external metabolites of the metabolic network from a)) with the measured concentrations of the components from c) was additionally carried out. Apart from proline, all concentrations measured by Baughman et al. are also taken into account in the metabolic network according to Niu et al. So as to be able to employ the measurement of the proline concentration, it would be possible either to use another simplified network that contains proline as an external metabolite, or it would be possible to expand the existing metabolic network.

Components that did in fact occur in the calculated macroreactions, but for which no data were available, were also ignored in the following. The corresponding rows of matrix K were accordingly deleted from the matrix. Deletion of the corresponding rows does not mean that these inputs or outputs are not used by the cell. They still exist in the metabolic network, but no measurements are available with which they can be reconciled. In this example, the inputs or outputs of arginine, glutamate, glycine, histidine, leucine, lysine, methionine, ammonium, oxygen, phenylalanine, serine, threonine, tryptophan, tyrosine and valine were ignored.

In the next steps of the method, the reduced matrix K—which represents the background knowledge—and the rates $\tilde{q}(t)$ from d) and the measured data from c)—which form the process know-how—are then used for obtaining a smallest possible subset L of the macroreactions from K.

The inventive "linear estimation of reaction rates of selected macroreactions" was used as quality criterion. As with the rates $\tilde{q}(t)$, the measured values of the cell count and of the antibody were normalized here to C-mol. This is necessary so that the dimension of the macroreactions agrees with those of the measured values.

The subset was selected with a genetic algorithm. In the calculation of the target function of this genetic algorithm, the linear optimization problem addressed in the "linear estimation of reaction rates of selected macroreactions" was solved. The final sum of the least error squares of the linear optimization problem calculated here was at the same time the value of the target function for the particular selection of the macroreactions.

For selecting the size of the subset L from K, optimization was carried out repeatedly with a different number of macroreactions in L. The number represents a compromise between the complexity of the model and the accuracy of reproduction. To determine how many reactions are sufficient for reproduction, either selection of the subset L may be repeated for a varying number of macroreactions, or a penalty term for the number of reactions can be added directly to the target function of the genetic algorithm. In this case several optimizations were carried out with a predefined number of macroreactions (10, 7, 5, 4 and 3). The minimum error found with the genetic algorithm is plotted in FIG. 9 against the number of macroreactions. It was found that in this case fewer than seven macroreactions are too few for representing the process course sufficiently well. The selected macroreactions are given in Table 3.

TABLE 3

Selected subset of the macroreactions (L). Components that are not underlined are not taken into account in the model, as no measurements are available for these.

0.474 Alanine + 0.474 Methionine
→ 0.158 Asparagine + 0.316 Aspartate + 0.632 Glycine + 0.158 Tryptophan
0.015 Alanine + 0.00789 Arginine + 0.0304 Asparagine + 0.0161 Glucose + 0.0236 Glutamine + 0.00375 Glutamate + 0.00366 Histidine + 0.00953 Isoleucine + 0.015 Leucine + 0.112 Methionine + 0.00626 Phenalanine + 0.0154 Serine + 0.0109 Valine
→ 0.963 X (Biomass) + 0.00276 Aspartate + 0.24 Glycine + 0.0208 Tryptophan
0.295 Asparagine + 0.147 Glutamate → 0.295 Aspartate + 0.885 Glycine + 0.147 Lactate
0.00753 □□□□□□□ + 0.113 □□□□□□□□ + 0.0603 □□□□□□ + 0.0225 □□□□□□□ + 0.0824 □□□□□□□ + 0.00909 □□□□□□□□ +
0.00597 □□□□□□□□□ + 0.0216 Tryptophan + 0.00431 □□□□□□□ + 0.0104 □□□□□
→ 0.918 □ (□□□□□□) + 0.061 □□□□□□□ + 0.0865 □□□□□□□□ + 0.343 □□□□□□ + 0.0631 □□□□□□□□
0.0654 Arginine + 0.412 Aspartate + 0.00991 Glucose + 0.0145 Glutamine + 0.554 Glycine + 0.00226 Histidine + 0.00588 Isoleucine + 0.00926 Leucine + 0.00706 Lysine + 0.0649 Phenalanine + 0.0095 Serine + 0.00671 Valine
→ 0.594 X (Biomass) + 0.049 Alanine + 0.395 Asparagine + 0.0503 Threonine + 0.0388 Tryptophan
0.0077 □□□□□□□ + 0.179 □□□□□□□□ + 0.0157 □□□□□□ + 0.104 □□□□□□□□ + 0.216 □□□□□□ + 0.00357 □□□□□□□ + 0.00929 □□□□□□□□ + 0.0146 □□□□□□ + 0.0112 □□□□□□ + 0.038 □□□□□□□ + 0.0106 □□□□□
→ 0.939 □ (□□□□□□) + 0.0624 □□□□□□ + 0.152 □□□□□□□□ + 0.0183 Tryptophan
0.0342 □□□□□□□ + 0.211 □□□□□□□□ + 0.00762 □□□□□□ + 0.0195 □□□□□□□ + 0.244 □□□□□□ + 0.00452 □□□□□□□ + 0.0546 □□□□□□□□ + 0.0185 □□□□□□□ + 0.0171 □□□□□□ + 0.00406 □□□□□□□□ + 0.0178 □□□□□□□ + 0.0203 □□□□□
→ 0.457 □ (□□□□□□) + 0.804 □□□ (□□□□□□□□) + 0.185 □□□□□□□□ + 0.0153 Tryptophan In the macroreactions shown, all external metabolites of the metabolic network from a) are indicated. However, only the underlined external metabolites form part of the model, as measured data from c) are only available for these.

6 Step f)

For the selected set of macroreactions, the reaction rates over time were determined. In this example, using the inventive method "linear estimation of reaction rates of selected macroreactions", the measured values shown in FIG. 10 were approximated by an estimation of the reaction rates $\underline{r}(t)$. The result of the method is a piecewise linear course of the individual (volumetric) reaction rates. By dividing by the interpolated course of the viable cell count $X_v(t)$, the cell-specific reaction rates $\underline{r}(t)$ of the macroreactions shown in Table 3 were obtained. The reaction rates $\underline{r}(t)$ thus obtained are shown in FIG. 10.

7 Step g)

For all macroreactions shown in Table 3, generic kinetics according to Formula 24 were assumed:

$$\hat{r}_k(t) = r_{k,max} \cdot \prod_{i=1}^{N_l} \tilde{r}_i(\underline{C}(t), \underline{p}, \dots) \qquad \text{(Formula 24)}$$

In this case, they were realized by Monod kinetics, i.e. for each reaction k for each substrate i, a limitation according to Formula 25:

$$\tilde{r}_i(t) = \left(\frac{C_i}{K_{m,k,i} + C_i(t)}\right)^{n_i} \qquad \text{(Formula 25)}$$

was introduced. Here, $r_{k,max}$ is the maximum reaction rate, $N_l$ is the number of limitations taken into account, $C_i$ is the concentration of the component i, $K_{m,k,i}$ are the associated Monod constants and $n_i$ is the Hill parameter for the reaction order. Their values are adjusted in steps h) and j).

Further terms are found from the analysis of the reaction rates $\underline{r}(t)$ from f). In this example, in addition to substrate limitations, inhibitions according to Formula 26 were also taken into account.

$$\tilde{r}_i = \left(\frac{K_{I,k,i}}{K_{I,k,i} + C_i}\right)^{n_i} \qquad \text{(Formula 26)}$$

For this limitation too, it was necessary to adjust the values of the parameters $K_{I,k,i}$ and $n_i$. The kinetic terms used for the reactions are given in Table 4.

TABLE 4

Kinetic terms of the selected macroreactions from L $$\hat{r}_1(t) = r_{1,max} \cdot \left(\frac{[\text{Ala}](t)}{K_{m,Ala,1} + [\text{Ala}](t)}\right) \cdot$$

$$\left(\frac{[\text{Glc}](t)}{K_{m,Glc,1} + [\text{Glc}](t)}\right)^2 \cdot \left(\frac{K_{I,Asn,1}}{K_{I,Asn,1} + [\text{Asn}](t)}\right)^2$$

$$\hat{r}_2(t) = r_{2,max} \cdot \left(\frac{[\text{Glc}](t)}{K_{m,Glc,2} + [\text{Glc}](t)}\right) \cdot \left(\frac{[\text{Gln}](t)}{K_{m,Gln,2} + [\text{Glc}](t)}\right) \cdot$$

$$\left(\frac{[\text{Asn}](t)}{K_{m,Asn,2} + [\text{Asn}](t)}\right) \cdot \left(\frac{[\text{Ala}](t)}{K_{m,Ala,2} + [\text{Ala}](t)}\right)^2$$

$$\hat{r}_3(t) = r_{3,max} \cdot \left(\frac{[\text{Glc}](t)}{K_{m,Glc,3} + [\text{Glc}](t)}\right) \cdot$$

$$\left(\frac{[\text{Asn}](t)}{K_{m,Glc,3} + [\text{Asn}](t)}\right) \cdot \left(\frac{K_{I,Lac,3}}{K_{I,Lac,3} + [\text{Lac}](t)}\right)^2$$

TABLE 4-continued

Kinetic terms of the selected macroreactions from L $$\hat{r}_4(t) = r_{4,max} \cdot \left(\frac{[Glc](t)}{K_{m,Glc,4} + [Glc](t)}\right) \cdot \left(\frac{[Gln](t)}{K_{m,Gln,4} + [Gln](t)}\right) \cdot$$
$$\left(\frac{[Asn](t)}{K_{m,Asn,4} + [Asn](t)}\right) \cdot \left(\frac{[X_t](t)}{K_{m,Xt,4} + [X_t](t)}\right)$$

$$\hat{r}_5(t) = r_{5,max} \cdot \left(\frac{[Glc](t)}{K_{m,Glc,5} + [Glc](t)}\right) \cdot \left(\frac{[Glc](t)}{K_{m,Gln,5} + [Gln](t)}\right) \cdot$$
$$\left(\frac{[Asp](t)}{K_{m,Asp,5} + [Asp](t)}\right) \cdot \left(\frac{K_{I,Asp,5}}{K_{I,Asp,5} + [Asp](t)}\right)^3 \cdot \left(\frac{K_{I,Asn,5}}{K_{I,Asn,5} + [Asn](t)}\right)$$

$$\hat{r}_6(t) = r_{6,max} \cdot \left(\frac{[Glc](t)}{K_{m,Glc,6} + [Glc](t)}\right) \cdot \left(\frac{[Gln](t)}{K_{m,Gln,6} + [Gln](t)}\right) \cdot$$
$$\left(\frac{[Asp](t)}{K_{m,Asp,6} + [Asp](t)}\right)^2$$

$$\hat{r}_7(t) = r_{7,max} \cdot \left(\frac{[Glc](t)}{K_{m,Glc,7} + [Glc](t)}\right) \cdot \left(\frac{[Gln](t)}{K_{m,Gln,7} + [Gln](t)}\right) \cdot$$
$$\left(\frac{[Asp](t)}{K_{m,Asp,7} + [Asp](t)}\right)$$

8 Step h)

For each reaction rate, the course of the reaction rate $\hat{r}_i(\underline{p}, \underline{C}^{int}(t))$ could be calculated algebraically with the kinetics given in Table 4 and the interpolated values of the concentrations $\underline{C}^{int}(t)$ taken into account in the kinetics.

The parameters of these kinetics were adjusted separately for each reaction i to the reaction rate $r_i(t)$ determined in step f). The target function for optimization of the parameters occurring in reaction i was in this example:

$$\min_{\underline{p}_k} \left( \sum_{l=0}^{T} \left( \hat{r}_k(\underline{p}_k, \underline{C}^{int}(t_l)) - r_k(t_l) \right)^2 \right) \quad \text{(Formula 27)}$$

The courses of all calculated $\hat{r}_k(\underline{p}_k, \underline{C}^{int}(t))$ adjusted in this way are shown together with the corresponding $r_k(t)$ in FIG. 11. The courses of the former are shown with dashes, and those of the latter are shown with solid lines. It can be seen that the course agrees qualitatively. This means that with the selected kinetics, the dynamics of the process can also be reproduced satisfactorily. This information is very useful in this modelling step, because if reproduction is unsatisfactory, the quick steps g) (selection of other kinetics) and h) (estimation of parameter values) can be repeated, until the desired degree of adjustment is reached. Thus, step i) was not necessary here.

9 Step j)

Further adjustment of the model parameter values $\underline{p}$ was carried out with the measured data from c). For this, all parameters were optimized at the same time. Moreover, the processes of apoptosis and lysis, which have not been examined previously, were also included. These are required in the differential equations that describe the development of the viable cell count and total cell count:

$$\frac{dX_v}{dt} = (\mu_x - \mu_d) \cdot X_v \quad \text{(Formula 28)}$$

$$\frac{dX_t}{dt} = \mu_x \cdot X_v - K_l \cdot (X_t - X_v) \quad \text{(Formula 29)}$$

The selected kinetics for describing apoptosis was:

$$\mu_d(t) = \mu_{d,max} \cdot \frac{([Lac](t) - C_{Lac,cr})}{K_{d,Lac} + ([Lac](t) - C_{Lac,cr})}, \quad \text{(Formula 30)}$$
$$[Lac] \geq C_{Lac,cr}$$

$$\mu_d(t) = 0, \quad \text{(Formula 31)}$$
$$[Lac] < C_{Lac,cr}$$

The lysis rate $K_l$ was assumed to be constant over the process. In addition to the parameters of the reaction rates, the parameters $C_{Lac,cr}$ (critical lactate concentration), $\mu_{d,max}$ (maximum death rate), $K_{d,Lac}$ (Monod parameter for describing the influence of the lactate concentration on the death rate) and $K_l$ (lysis rate) introduced by apoptosis and lysis were determined in this step. In the example, the course of the estimated concentrations $\underline{\hat{C}}(t)$ was determined from the starting values of the data set, by numerical solution of the ODE system. The difference between the measured concentrations $\underline{C}^m(t)$ and the estimated concentrations $\underline{\hat{C}}(t)$ was minimized by usual methods with the following target function:

$$\min_{\underline{p}} \left( \sum_{i=1}^{n_{comp}} \left( \sum_{l=0}^{T} \left( \hat{C}_i(\underline{p}, t_l) - C_i^m(t_l) \right)^2 \right) \right) \quad \text{(Formula 32)}$$

With a total of 33 parameters $\underline{p}$, as a rule this optimization is difficult to perform, as the target function has many local optima. If a deterministic optimization algorithm is started, for example the Levenberg-Marquardt algorithm on the starting values of the parameters known from step h), there is a much greater chance of success. The adjusted process course is shown in FIG. 12. The adjusted parameters are shown in Table 5.

TABLE 5

Parameters of the kinetics and of apoptosis and lysis

| | |
|---|---|
| $K_{m,Glc,1}$ | 14.6 |
| $K_{m,Ala,1}$ | 3.41 |
| $K_{m,Glc,2}$ | 0.0508 |
| $K_{m,Gln,2}$ | 0.00881 |
| $K_{m,Asn,2}$ | 1.38 |
| $K_{m,Ala,2}$ | 2.19 |
| $K_{m,Glc,3}$ | 7.13 |
| $K_{m,Asn,3}$ | 6.84 |
| $K_{m,Xt,4}$ | 0.0315 |
| $K_{m,Glc,4}$ | 1.29 |
| $K_{m,Gln,4}$ | 2.19 |
| $K_{m,Asn,4}$ | 1.68 |
| $K_{m,Glc,5}$ | 100 |
| $K_{m,Gln,5}$ | 28.2 |
| $K_{m,Asp,5}$ | 102 |
| $K_{m,Glc,6}$ | 0.0451 |
| $K_{m,Gln,6}$ | 0.791 |
| $K_{m,Asp,6}$ | 1.06 |
| $K_{m,Gln,7}$ | 0.0187 |
| $K_{m,Asp,7}$ | 0.872 |

TABLE 5-continued

Parameters of the kinetics and of apoptosis and lysis

| | |
|---|---|
| $\gamma_{1,max}$ | 9.47 |
| $\gamma_{2,max}$ | 9.91 |
| $\gamma_{3,max}$ | 57.6 |
| $\gamma_{4,max}$ | 21.7 |
| $\gamma_{5,max}$ | 0.345 |
| $\gamma_{6,max}$ | 49.4 |
| $\gamma_{7,max}$ | 3.03 |
| $K_{I Asn,1}$ | 16.1 |
| $K_{I Lac,3}$ | 0.681 |
| $K_{I Asp,5}$ | 9.74 |
| $K_{I Asn,5}$ | 1.10 |
| $\mu_{d,max}$ | 0.125 |
| $K_{d,Lac}$ | 1.01 |
| $C_{Lac,cr}$ | 1.22 |
| $K_t$ | 0.00843 |
| $K_{m,Glc,7}$ | 0.0145 |

10 Step k)

The model, consisting of the matrix L, the kinetics from Table 4 and the kinetics of apoptosis with the associated parameter values from Table 5, was produced as the output.

LIST OF SYMBOLS

| | |
|---|---|
| _ (underline) | denotes a vector |
| $_i$ (subscript i) | denotes the i-th element of a vector |
| $_k$ (subscript k) | denotes the k-th element of a vector |
| [ ] | denotes the concentration of the component in brackets |
| C | concentration |
| ΔC | concentration difference |
| $C^{Int}$ | interpolated concentration |
| $\hat{C}$ | estimated concentration (e.g. by solving a differential equation) |
| $C_s$ | shifted concentration |
| $C_{cr}$ | critical concentration |
| $C^m$ | measured concentration |
| D | dilution rate |
| q | determined cell-specific secretion and uptake rate |
| $\tilde{q}$ | determined cell-specific secretion and uptake rate that has been converted from any unit to $\left[\frac{\text{Substance amount}}{\text{Time} \cdot \text{Cell count}}\right]$ |
| r | determined reaction rate |
| $\hat{r}$ | estimated reaction rate (e.g. by calculating reaction kinetics) |
| $\tilde{r}$ | limitation of kinetics |
| $r_{max}$ | parameter of reaction kinetics |
| N | stoichiometric matrix |
| $N_p$ | external stoichiometric matrix |
| K | matrix that contains macroreactions |
| E | matrix that contains all elementary modes |
| $X_t$ | total cell count |
| $X_v$ | viable cell count |
| $\mu$ | growth rate |
| $\mu_d$ | death rate |
| $\tilde{\mu}$ | growth rate that has been converted from any unit to $\left[\frac{\text{Substance amount}}{\text{Time} \cdot \text{Cell count}}\right]$ |
| $K_d$ | lysis rate |
| $K_I$ | parameter of an inhibition limitation |
| $K_M$ | parameter of a substrate limitation |
| n | Hill parameter of an inhibition or substrate limitation |
| L | subset of the macroreactions that is used for the model |
| p | model parameter |
| S | substrate |
| $SSR_q$ | sum of squared residuals of the specific uptake or release rates |
| $SSR_c$ | sum of squared residuals of the concentration |
| $SSR_r$ | sum of squared residuals of the reaction rates |

The rate $q_{MAB}$ is given in $$\left[\frac{10^{-4} mM}{h \cdot 10^9 \text{Cells}}\right].$$

Figure 1:
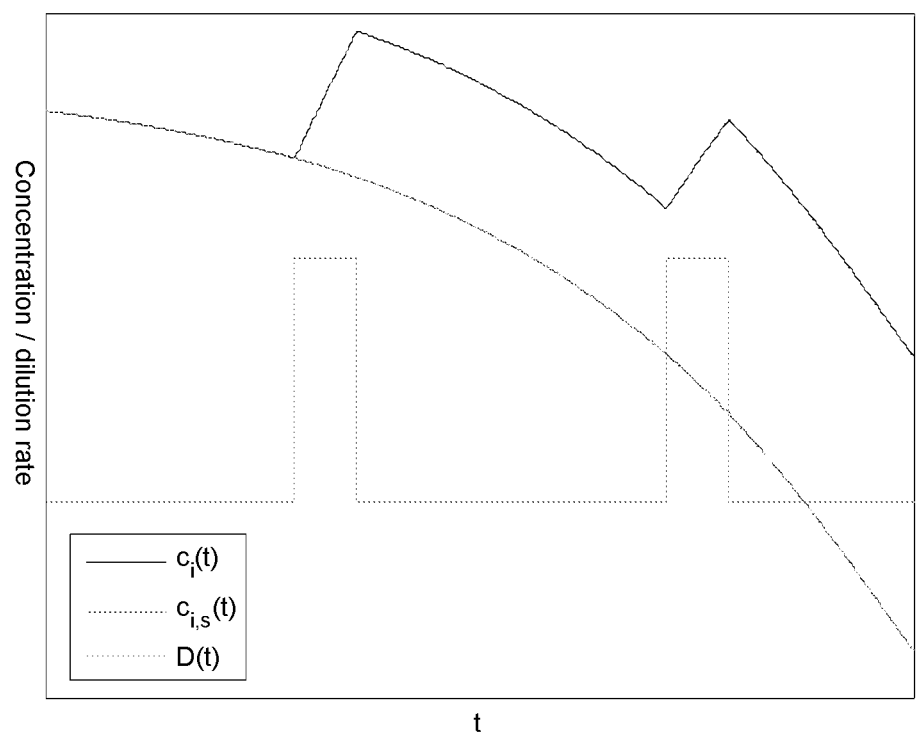
FIG. 1 shows the shift of measured data: It shows the actual course of a measured quantity ($C_i(t)$), which changes suddenly when there are changes of the dilution rate (D(t)). The shifted course ($C_{i,s}(t)$) only arises because of changes caused by the cell.
Figure 2:
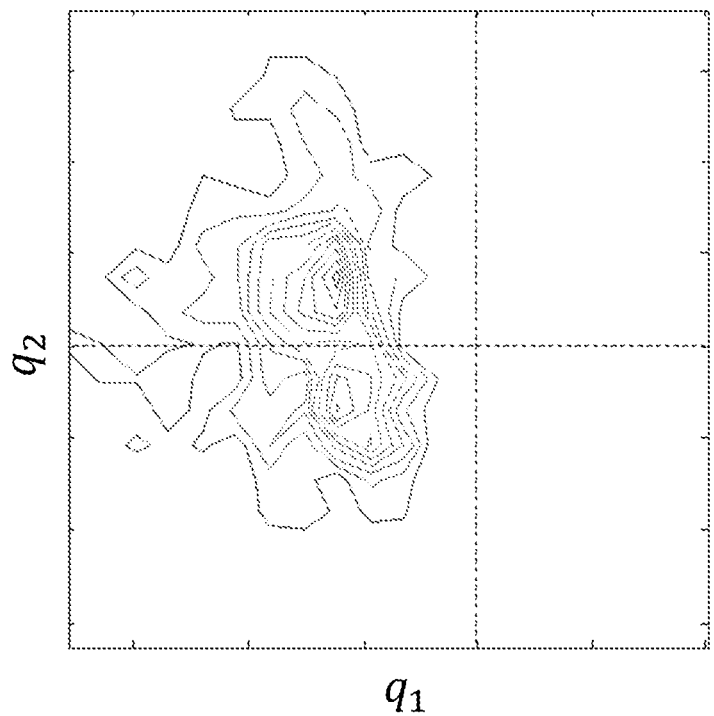
FIG. 2 shows the flux map of two specific rates $q_1$ and $q_2$. The contour lines indicate the frequency with which the particular combination of the rates occurs in the measured data.
Figure 3:
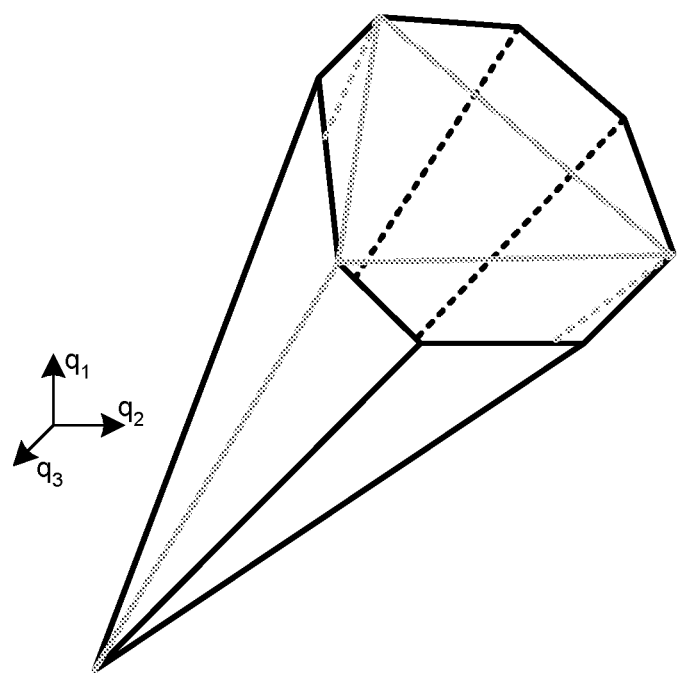
FIG. 3 shows a three-dimensional representation of the solution space, which is spanned by a positive linear combination of EMs. The solution space of the complete set is shown in black, and that of a subset is shown in grey.
Figure 4:
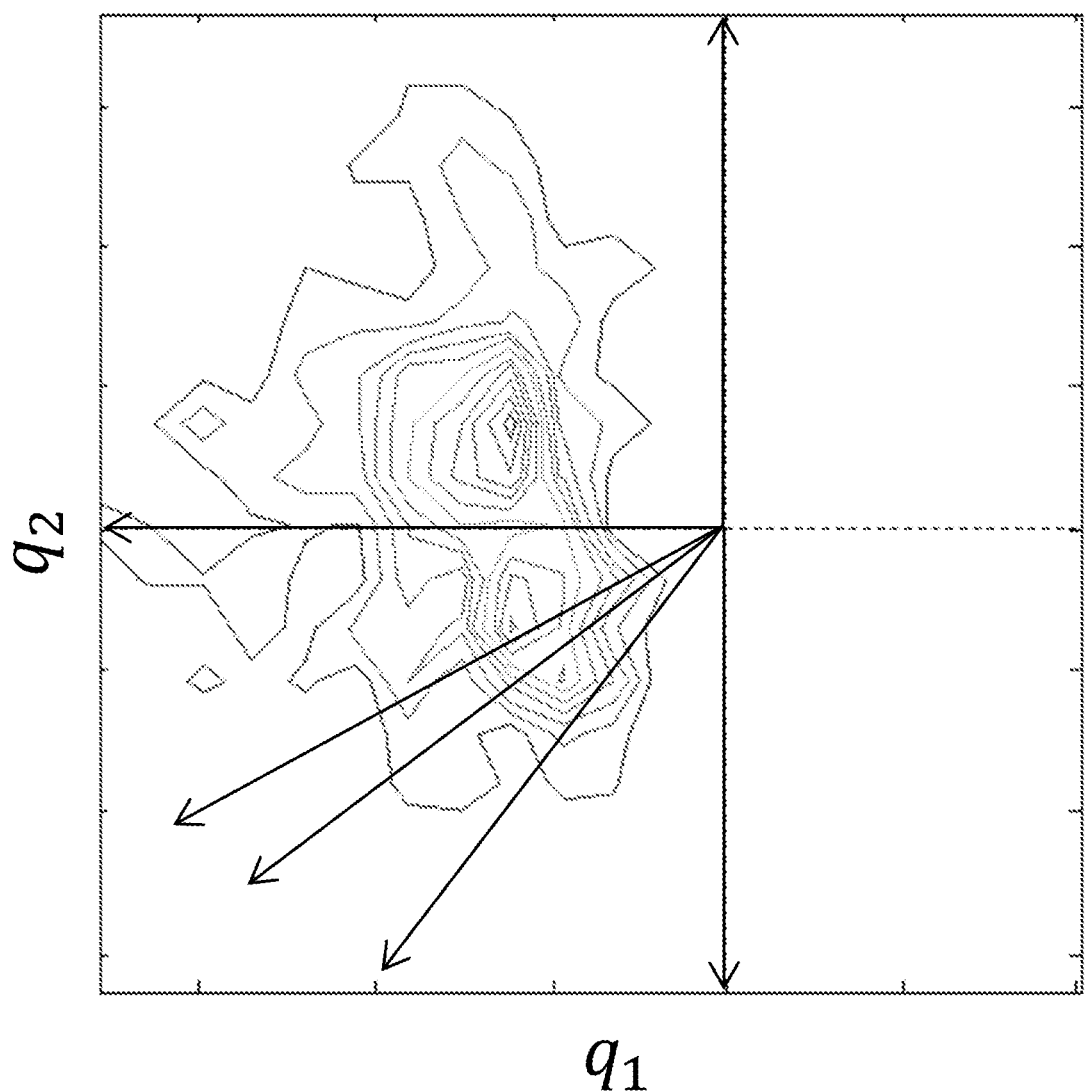
FIG. 4 shows the flux map of two specific rates $q_1$ and $q_2$. The 2-dimensional projections of the macroreactions of a set L are shown as vectors.
Figure 5:
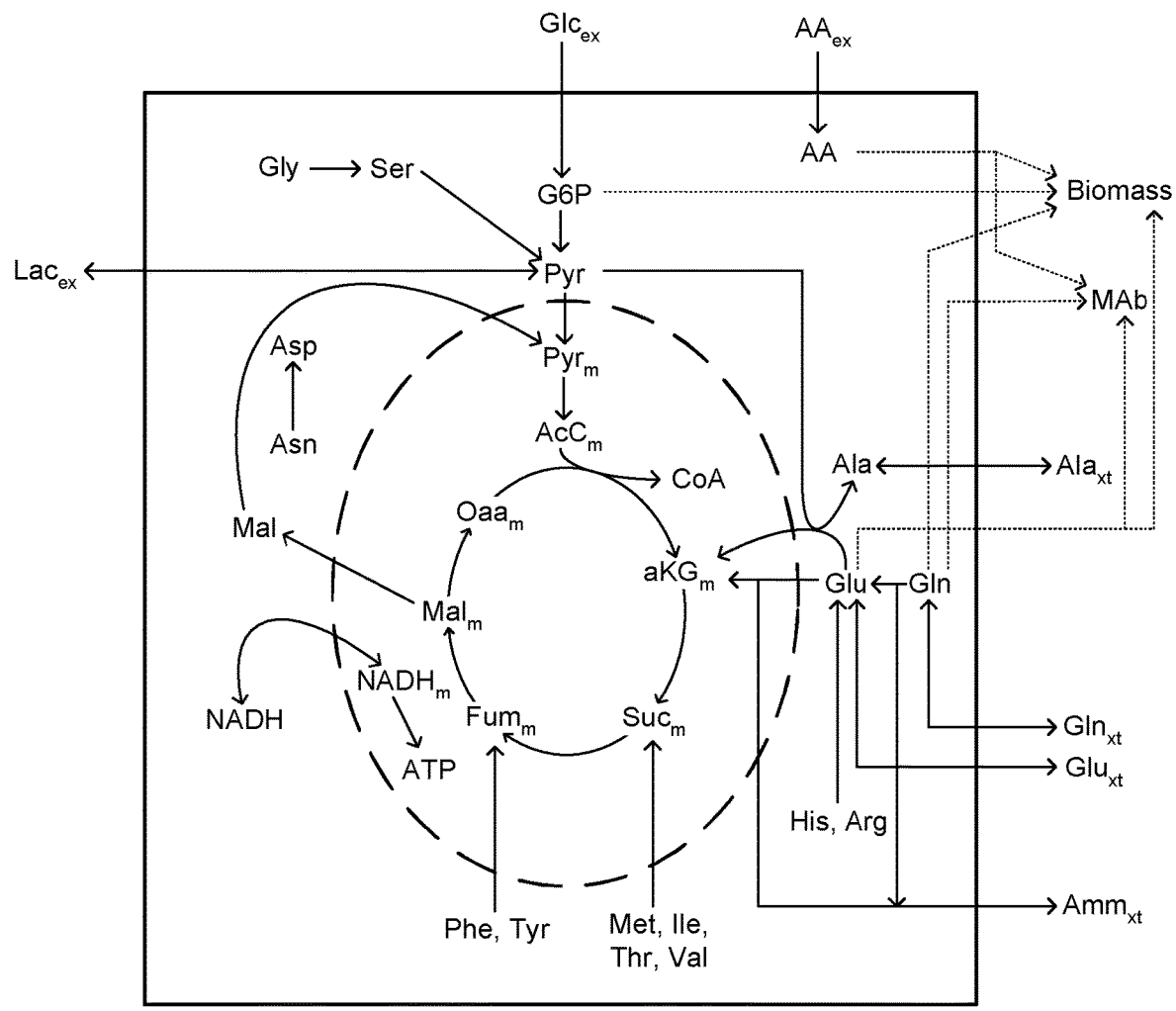
FIG. 5 shows a schematic representation of the metabolic network from Niu et al. Here, the boundary of the cell is shown as a box. The intracellular border of the mitochondrium is shown with a dashed line. External components are marked with the subscript "xt". The arrows and dotted arrows denote reactions.
Figure 6:
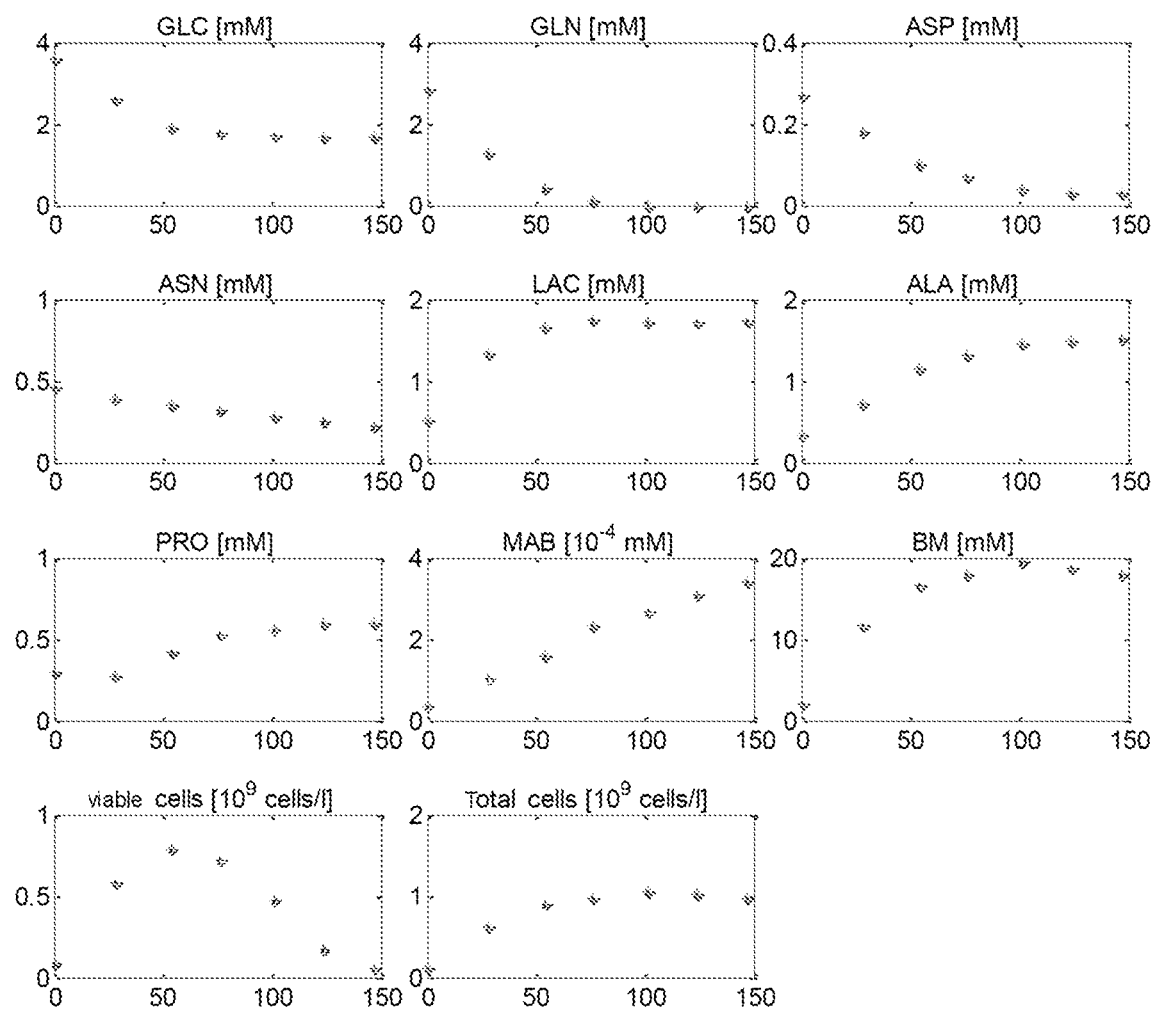
FIG. 6 shows the measured data of a fermentation with hybridoma cells from Baughman et al. The total cell count (total cells) is calculated here from the total of viable cells and dead cells. The abbreviations GLC, GLN, ASP, ASN, LAC, ALA and PRO denote the substrate glucose and the amino acids glutamine, aspartic acid, asparagine, alanine and proline and the metabolic product lactate. The abbreviation MAB denotes the product of monoclonal antibodies and BM denotes biomass.
Figure 7:
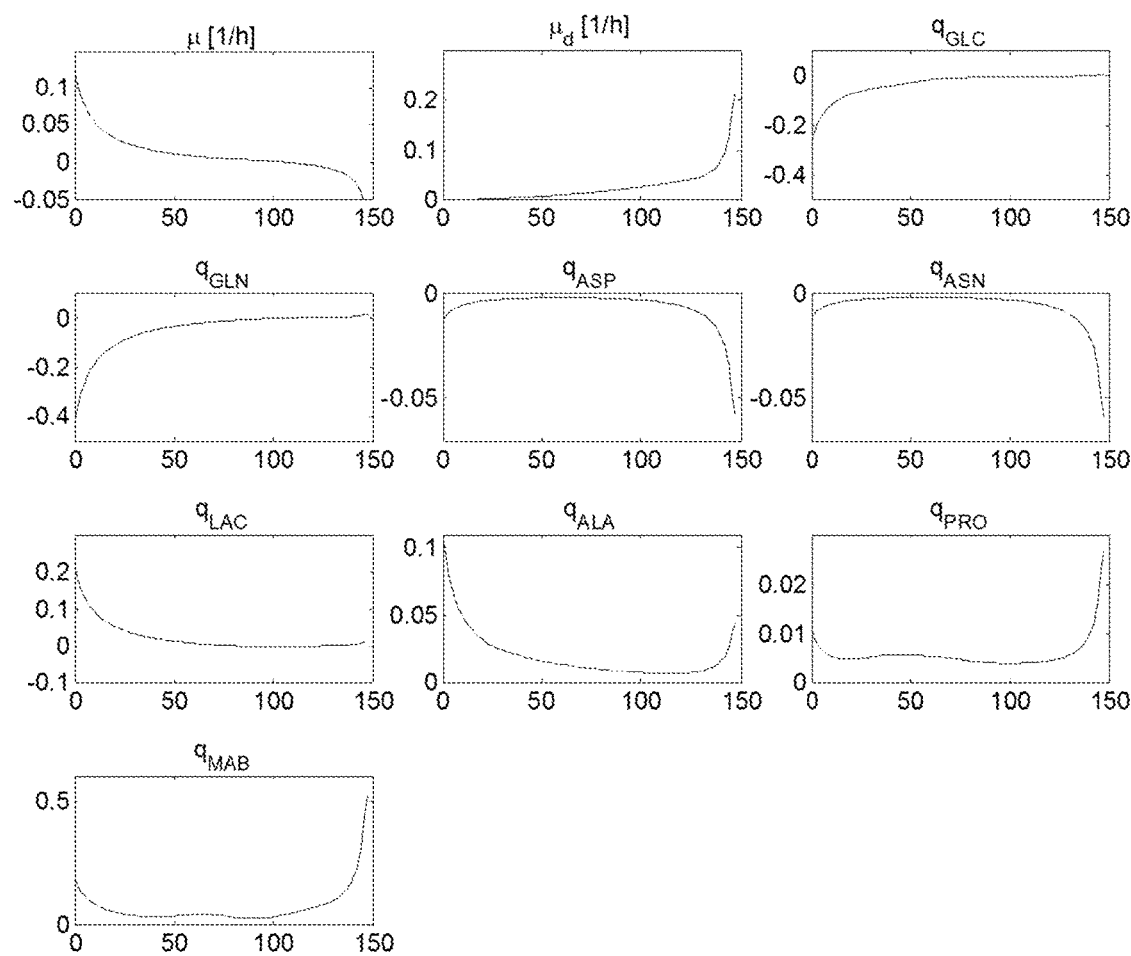
FIG. 7 shows the growth and death rates and the cell-specific uptake and secretion rates. All cell-specific rates except $q_{MAB}$ are given in $$\left[\frac{mM}{h \cdot 10^9 \text{Cells}}\right].$$
Figure 8:
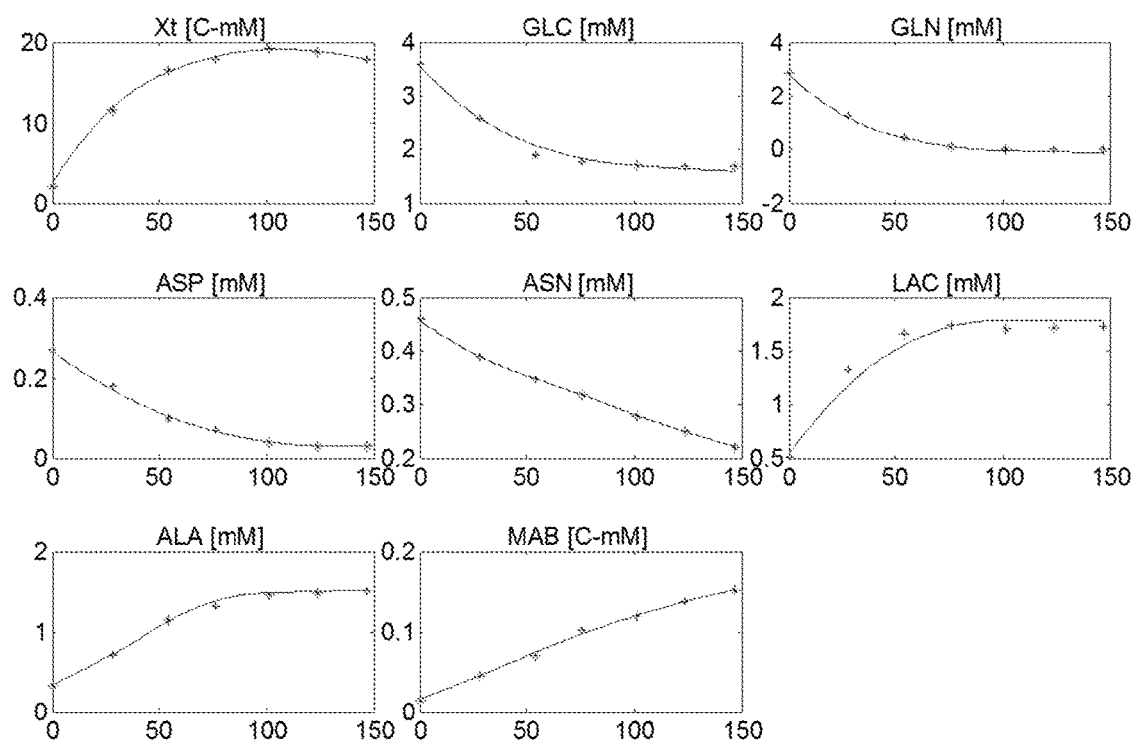

FIG. 8 shows the concentrations approximated with the "linear estimation of reaction rates of selected macroreactions" with the selected reaction set. The total cell count ($X_t$) and the antibody concentration (MAB) were converted for this to C-mol.

Figure 9:
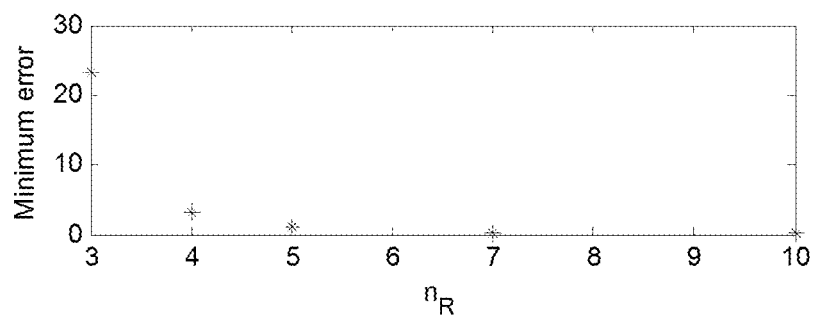

FIG. 9 shows the minimum error plotted against the number of macroreactions in the subset ($n_R$).

Figure 10:
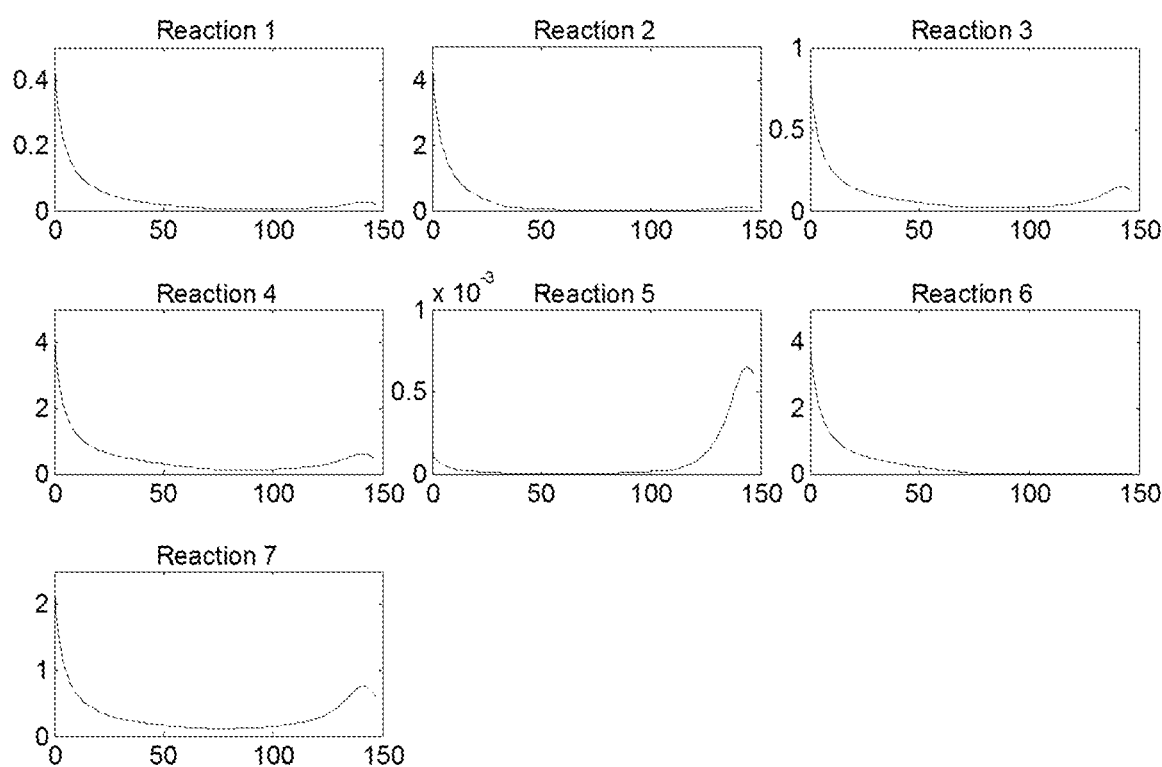

FIG. 10 shows the reaction rates of the macroreactions $\underline{r}(t)$ determined with the inventive method "linear estimation of reaction rates of selected macroreactions".

Figure 11:
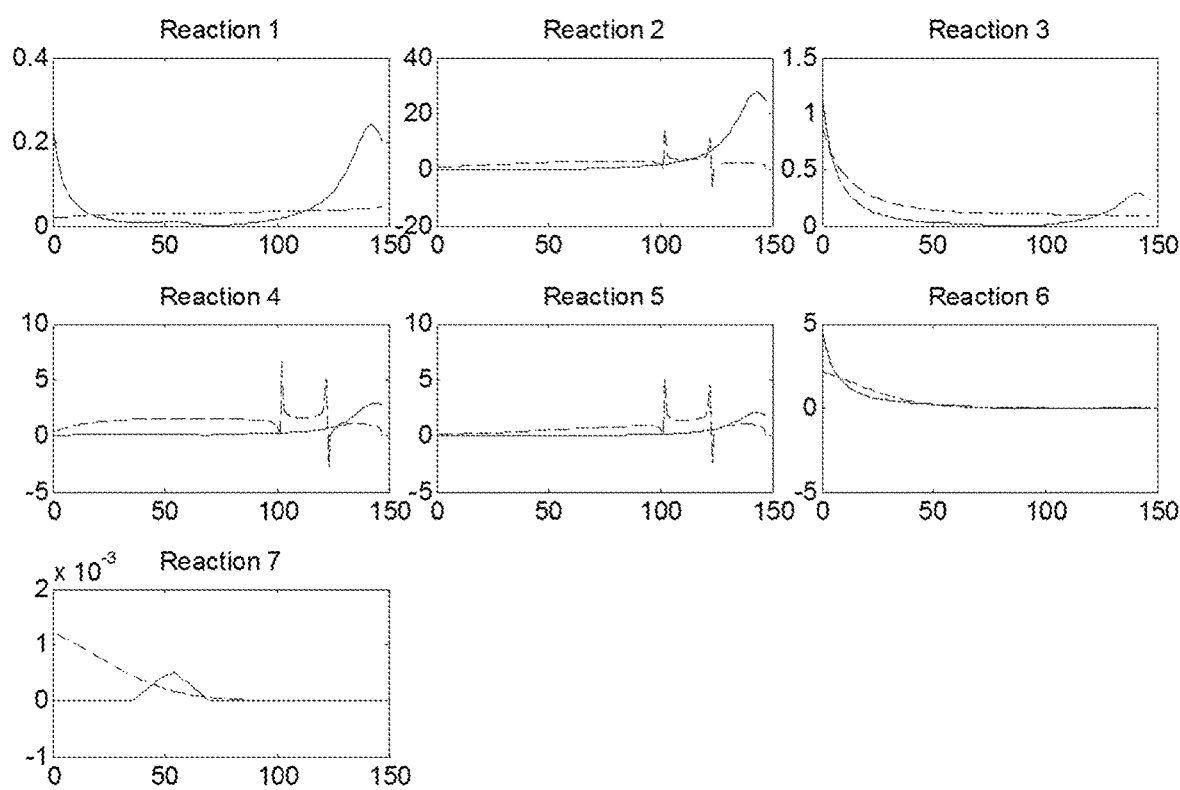

FIG. 11 shows the reaction rates of the macroreactions $\underline{r}(t)$ determined with the inventive method "linear estimation of reaction rates of selected macroreactions" (solid line) together with the algebraically calculated reaction rates $\hat{\underline{r}}(\underline{p}, \underline{C}^{int}(t))$ (dashed line).

Figure 12:
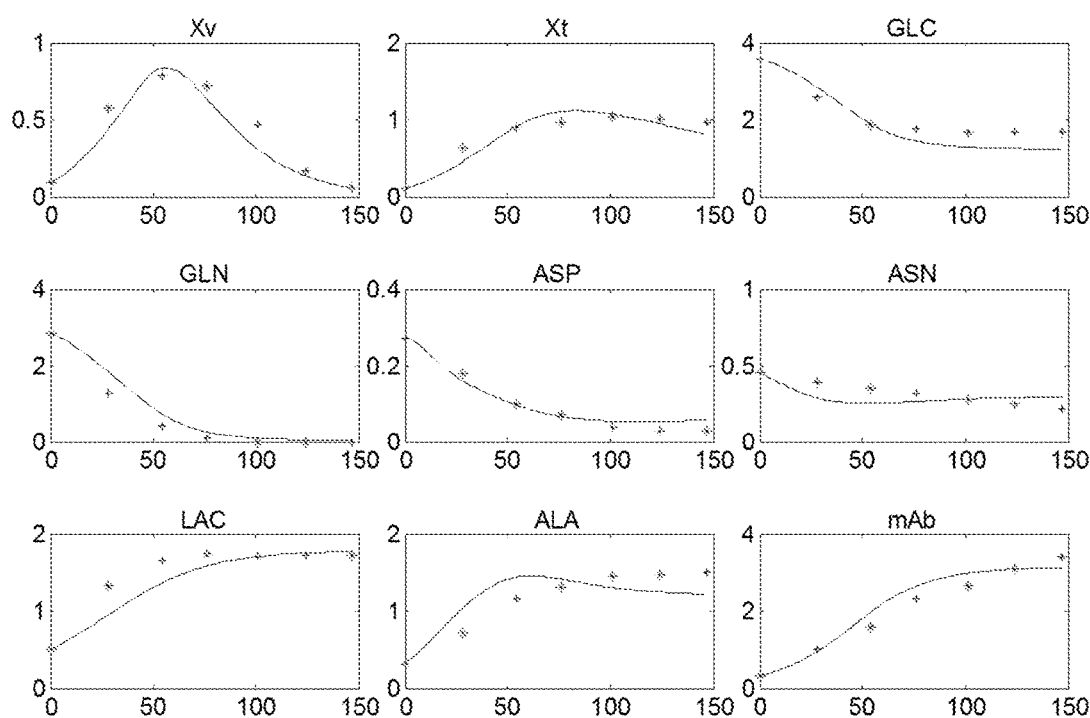

FIG. 12 shows a comparison of the measured concentrations $\underline{C}^m(t)$ (points) and the simulated process course $\hat{\underline{C}}(t)$ (solid line). The concentrations are given in [mM]. The viable cell count and total cell count ($X_v/X_t$ in [$10^9$ cells/l]) and the concentration of the antibody (mAb in [$10^{-4}$ mM]) are exceptions.

The invention claimed is:

1. A computer-implemented method for model-based estimation of the state of a bioreaction with an organism in a bioreactor comprising:
   creating a model of a bioreaction with an organism, said model including a matrix L, kinetics of macroreactions and model parameters of calculated values, which comprises the following steps:
   a. defining selected metabolic pathways of the organism, their properties of stoichiometry and reversibility as background knowledge and calculating elementary modes from this input;
   b. combining the elementary modes from a) in a matrix K, wherein the elementary modes combine the metabolic pathways from a) in macroreactions and the matrix K contains the stoichiometry and reversibility properties of all macroreactions;
   c. entering measured data for the bioreaction with the organism;
   d. calculating, using an interpolation method, specific rates for the organism of the metabolic pathways based on the measured data entered from c);
   e. selecting relevant macroreactions as a subset r(t) of the elementary modes from a) by
      i. data-independent and/or data-dependent prereduction of the elementary modes from a);
      ii. selection of the subset from the prereduction from e) i. using the measured data from c) and/or one or more rates from d) by means of an algorithm according to a mathematical quality criterion and combination of the subset in a matrix L;
      iii. optionally, the subset is shown graphically,
   f. calculating, using an interpolation method, reaction rates of the macroreactions of the subset r(t) on the basis of the measured data from c) and/or the rates from d);
   g. devising kinetics of the macroreactions of the subset from e) ii. using the following intermediate steps:
      i. devising generic kinetics from the stoichiometry of the macroreactions from e);
      ii. determining factors influencing the macroreactions from e) from the reaction rates from f);
      iii. expanding the generic kinetics from g) i. by model parameter values which quantify the factors determined in g) ii;
   h. performing separately for each macroreaction, a first adjustment of the model parameter values of the model parameters of g) iii to the calculated reaction rates from f);
      i. optionally repeating steps g) and h) until a predefined quality of adjustment is reached;
   j. adjusting the model parameter values of the model parameters of g) iii, h) or i) to the measured data from c);
   k. forming the matrix L from e) ii, the kinetics from g) iii and the model parameter values of the model parameters from j) as an output for transferring to a process control module or process development module; and
   closed-loop controlling the bioreaction using the output of step k),
   outputting the estimated state of the bioreaction.

2. The computer-implemented method according to claim 1, wherein in step d), growth rates of the organism, and most preferably also death rates of the organism are calculated.

3. The computer-implemented method according to claim 1, wherein in step g), an individual adjustment of the kinetics takes place, based on an analysis of the reaction rates from f).

4. The computer-implemented method according to claim 1, wherein in step h), the adjustment of the parameter values of the kinetics from g) takes place by combining several methods of adjustment.

5. The computer-implemented method according to claim 1, wherein in step e) ii., for selecting the subset of the macroreactions, linear estimation of reaction rates of selected macroreactions is carried out.

6. The computer-implemented method according to claim 1, wherein in step e) ii., for selecting the subset of macroreactions, linear estimation of reaction rates of selected macroreactions is carried out in combination with an evolutionary algorithm.

7. The computer-implemented method according to claim 1, wherein the measured data are shifted before using the interpolation method in step d), in order to achieve the description of constant consumption without feed peaks.

8. The computer-implemented method according to claim 1, wherein in step f), linear estimation of reaction rates of selected macroreactions is carried out.

9. The computer-implemented method according to claim 1, wherein in step e) i., a data-dependent prereduction is carried out and the method of linear estimation of reaction rates of selected macroreactions with NNLS is used for this.

10. The computer-implemented method according to claim 1, wherein in step e) iii., validity of selection of the subset of macroreactions is tested by means of a flux map.

11. The computer-implemented method according to claim 1, wherein in step e) ii., the selection from the prereduction from e) i. is carried out using the measured data from c).

12. The computer-implemented method according to claim 1, wherein the method is executed by a computer program.

13. The computer-implemented method according to claim 1, wherein the method is executed by a software program.

* * * * *